(12) United States Patent
Schwerdtfeger et al.

(10) Patent No.: US 9,970,869 B2
(45) Date of Patent: May 15, 2018

(54) USE OF TURBIDIMETER FOR MEASUREMENT OF SOLID CATALYST SYSTEM COMPONENT IN A REACTOR FEED

(71) Applicant: Chevron Phillips Chemical Company LP, The Woodlands, TX (US)

(72) Inventors: Eric D. Schwerdtfeger, Bartlesville, OK (US); Daniel G. Hert, Owasso, OK (US); Max P. McDaniel, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 338 days.

(21) Appl. No.: 14/809,147

(22) Filed: Jul. 24, 2015

(65) Prior Publication Data

US 2017/0023474 A1    Jan. 26, 2017

(51) Int. Cl.
*G01N 21/53* (2006.01)
*G01N 15/06* (2006.01)
(Continued)

(52) U.S. Cl.
CPC ........ *G01N 21/532* (2013.01); *B01J 19/1837* (2013.01); *B01J 21/16* (2013.01);
(Continued)

(58) Field of Classification Search
None
See application file for complete search history.

(56) References Cited

U.S. PATENT DOCUMENTS 2,930,784 A * 3/1960 Hanson ................. B01D 43/00
                                                  502/235
2,962,926 A * 12/1960 Marak ..................... G01N 21/27
                                                  250/204
(Continued)

OTHER PUBLICATIONS

Cotton, F. Albert, et al., "Advanced Inorganic Chemistry," Sixth Edition, cover page, title page, pp. ix-x, and book description, Mar. 30, 1999, John Wiley & Sons, Inc.
(Continued)

*Primary Examiner* — Paul West
*Assistant Examiner* — Mark A Shabman
(74) *Attorney, Agent, or Firm* — Conley Rose, P.C.; Rodney B. Carroll; Monte R. Rhodes

(57) ABSTRACT

A method of monitoring a solid component of a reactor feed stream in a polymer production system, comprising (a) measuring a turbidity of the reactor feed stream, wherein the reactor feed stream comprises a solid component of a polymerization catalyst system, and (b) translating the turbidity of the reactor feed stream into a concentration of the solid component in the reactor feed stream. A method of monitoring a solid component of a reactor feed stream in a polymer production system, comprising (a) measuring a turbidity of a precontactor feed stream, wherein the precontactor feed stream comprises a solid component of a polymerization catalyst system, and (b) translating the turbidity of the precontactor feed stream into a concentration of the solid component in a precontactor effluent stream, wherein the precontactor effluent stream comprises the reactor feed stream.

21 Claims, 11 Drawing Sheets

(51) Int. Cl.
    *B01J 19/18* (2006.01)
    *B01J 21/16* (2006.01)
    *C08F 2/00* (2006.01)
    *G01N 21/82* (2006.01)
    *G01N 21/85* (2006.01)
    *G01N 21/84* (2006.01)

(52) U.S. Cl.
    CPC .............. *C08F 2/00* (2013.01); *G01N 15/06* (2013.01); *G01N 21/82* (2013.01); *G01N 21/85* (2013.01); *G01N 2015/0693* (2013.01); *G01N 2021/8416* (2013.01); *G01N 2201/062* (2013.01); *G01N 2201/08* (2013.01)

(56) References Cited

U.S. PATENT DOCUMENTS

| | | | |
|---|---|---|---|
| 3,248,179 | A | 4/1966 | Norwood |
| 3,976,632 | A | 8/1976 | Delap |
| 4,060,480 | A | 11/1977 | Reed et al. |
| 4,310,440 | A | 1/1982 | Wilson et al. |
| 4,452,910 | A | 6/1984 | Hopkins et al. |
| 4,501,885 | A | 2/1985 | Sherk et al. |
| 4,588,790 | A | 5/1986 | Jenkins, III et al. |
| 4,619,901 | A | 10/1986 | Webb et al. |
| 4,801,204 | A | 1/1989 | Nakamura et al. |
| 4,940,571 | A | 7/1990 | Su et al. |
| 5,089,667 | A | 2/1992 | Goussin et al. |
| 5,352,749 | A | 10/1994 | DeChellis et al. |
| 5,376,611 | A | 12/1994 | Shveima |
| 5,436,304 | A | 7/1995 | Griffin et al. |
| 5,565,175 | A | 10/1996 | Hottovy et al. |
| 5,575,979 | A | 11/1996 | Hanson |
| 6,239,235 | B1 | 5/2001 | Hottovy et al. |
| 6,262,191 | B1 | 7/2001 | Hottovy et al. |
| 6,833,415 | B2 | 12/2004 | Kendrick et al. |
| 7,163,906 | B2 | 1/2007 | McDaniel et al. |
| 7,619,047 | B2 | 11/2009 | Yang et al. |
| 7,790,820 | B2 | 9/2010 | Jensen et al. |
| 7,803,324 | B2 | 9/2010 | Burns et al. |
| 7,884,163 | B2 | 2/2011 | McDaniel et al. |
| 7,960,487 | B2 | 6/2011 | Yang et al. |
| 2008/0295581 | A1* | 12/2008 | Zhang .................. G01N 21/78 73/61.43 |
| 2009/0088537 | A1* | 4/2009 | Yang ...................... C07F 17/00 526/64 |
| 2009/0163642 | A1 | 6/2009 | Kiss et al. |
| 2013/0217843 | A1 | 8/2013 | McDaniel et al. |

OTHER PUBLICATIONS

Hawley's Condensed Chemical Dictionary, Eleventh Edition, cover page, contents page, pp. 862-863, Van Nostrand Reinhold Company.
McNaught, Alan D., et al., "Compendium of Chemical Terminology," International Union of Pure and Applied Chemistry, Second edition, 1997, 5 pages of cover, publishing information, and contents, Wiley-Blackwell.
Pinnavaia, Thomas J., "Intercalated Clay Catalysts," Apr. 22, 1983, pp. 365-371, vol. 220, No. 4595, Science.
Thomas, J. M., "Sheet Silicate Intercalates: New Agents for Unusual Chemical Conversions," Intercalation Chemistry, 1982, Chapter 3, pp. 55-99, Academic Press, Inc.
International Application PCT/US2016/042938 Search Report dated Sep. 29, 2016.

* cited by examiner

USE OF TURBIDIMETER FOR MEASUREMENT OF SOLID CATALYST SYSTEM COMPONENT IN A REACTOR FEED

TECHNICAL FIELD

The present disclosure generally relates to the production of polyethylene. More specifically, this disclosure relates to a process for improving polyethylene production by monitoring the amount of catalyst (e.g., a solid component of a catalyst system) in a reactor.

BACKGROUND

The production of polymers such as polyethylene requires a catalyst system that enables polymerization of monomers (e.g., ethylene). The amount of each catalyst system component in a polymerization reactor is an important process parameter which can impact the outcome of the polymerization reaction (e.g., polymerization yield, and properties of the resulting polymer). When the catalyst system contains solid components, it can be difficult to accurately measure the amount of solid components fed to a polymerization reactor, in part due to the solid components being introduced to the reactor as a heterogeneous mixture (e.g., a solid component in a fluid mixture, such as a slurry). In some instances, the contents of the polymerization reactor can be sampled and analyzed to calculate how much catalyst system component(s) was present in the reactor, but such analysis does not generally provide for adjusting the amounts of catalyst system components in the reactor in real-time or near real-time. Thus, there is an ongoing need for developing processes for real-time monitoring of the amount of catalyst system components in a polymerization reactor (e.g., in a reactor feed stream).

BRIEF SUMMARY

Disclosed herein is a method of monitoring a solid component of a reactor feed stream in a polymer production system, comprising (a) measuring a turbidity of the reactor feed stream, wherein the reactor feed stream comprises a solid component of a polymerization catalyst system, and (b) translating the turbidity of the reactor feed stream into a concentration of the solid component in the reactor feed stream.

Also disclosed herein is a method of monitoring a solid component of a reactor feed stream in a polymer production system, comprising (a) measuring a turbidity of a precontactor feed stream, wherein the precontactor feed stream comprises a solid component of a polymerization catalyst system, and (b) translating the turbidity of the precontactor feed stream into a concentration of the solid component in a precontactor effluent stream, wherein the precontactor effluent stream comprises the reactor feed stream.

Further disclosed herein is a method of monitoring a solid component of a reactor feed stream in a polymer production system, comprising (a) measuring a turbidity of a precontactor effluent stream, wherein the precontactor effluent stream comprises the reactor feed stream, and (b) translating the turbidity of the precontactor effluent stream into a concentration of the solid component in the reactor feed stream.

BRIEF DESCRIPTION OF THE DRAWINGS

For a detailed description of the preferred embodiments of the disclosed processes and systems, reference will now be made to the accompanying drawings in which.

DETAILED DESCRIPTION

Figure 1:
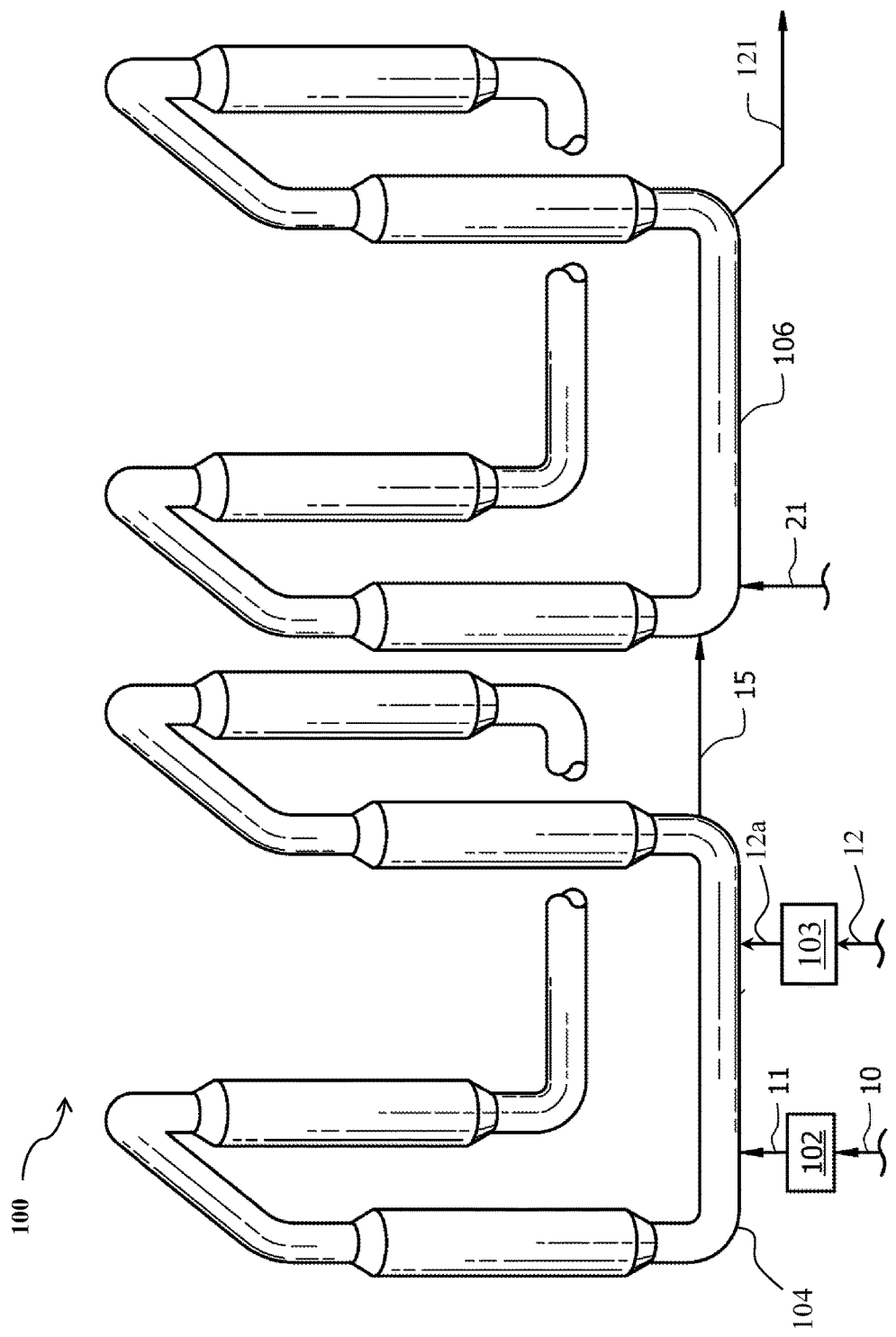
FIG. 1 illustrates a schematic of an embodiment of a loop slurry process.

It should be understood at the outset that although an illustrative implementation of one or more embodiments are provided below, the disclosed systems and/or methods can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

Disclosed herein are systems, apparatuses, and processes related to petrochemical production processes, for example the production of polyethylene. The systems, apparatuses, and processes are generally related to a method of monitoring a solid component of a reactor feed stream (e.g., a solid component of a polymerization catalyst system) in a petrochemical production process, for example the production of polyethylene.

In an embodiment, a method of monitoring a solid component of a reactor feed stream in a polymer production system (e.g., polyethylene production system) can generally comprise the steps of (a) measuring a turbidity of the reactor feed stream, wherein the reactor feed stream comprises a solid component of a polymerization catalyst system; and (b) translating the turbidity of the reactor feed stream into a concentration of the solid component in the reactor feed stream. Although the various steps of the methods disclosed herein can be disclosed or illustrated in a particular order, such should not be construed as limiting the performance of these methods to any particular order unless otherwise indicated.

In an embodiment, a method of monitoring the amount of each component of a polymerization catalyst system in a polymerization reactor in a polymer production system (e.g., polyethylene production system) can generally comprise monitoring the amount of each component of a polymerization catalyst system (e.g., a solid component, or a liquid component) in one or more reactor feed streams. While the present disclosure will be discussed in detail in the context of a method of monitoring a solid component of a polymerization catalyst system in a reactor feed stream in a polyethylene production system, it should be understood that such method or any steps thereof can be applied in any suitable petrochemical production process requiring monitoring a solid component of a reactor feed stream. The solid component can comprise any suitable solid component compatible with the disclosed methods and materials.

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art to which this invention belongs. Further, unless otherwise required by context, singular terms shall include pluralities and plural terms shall include the singular.

Unless explicitly stated otherwise in defined circumstances, all percentages, parts, ratios, and like amounts used herein are defined by weight.

Further, certain features of the present invention which are, for clarity, described herein in the context of separate embodiments, may also be provided in combination in a single embodiment. Conversely, various features of the invention that are, for brevity, described in the context of a single embodiment, may also be provided separately or in any sub-combination.

If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claim. A "consisting essentially of" claim occupies a middle ground between closed claims that are written in a "consisting of" format and fully open claims that are drafted in a "comprising" format. Absent an indication to the contrary, describing a compound or composition as "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a catalyst system consisting of specific components; alternatively, consisting essentially of specific components; or alternatively, comprising the specific components and other non-recited components.

In this disclosure, while systems, processes, and methods are often described in terms of "comprising" various components, devices, or steps, the systems, processes, and methods can also "consist essentially of" or "consist of" the various components, devices, or steps, unless stated otherwise.

The term "about" as used herein means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

The terms "contact product," "contacting," and the like, are used herein to describe compositions wherein the components are contacted together in any order, in any manner, and for any length of time, unless otherwise specified. For example, the components can be contacted by blending or mixing. Further, unless otherwise specified, the contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Likewise, "contacting" two or more components can result in a reaction product or a reaction mixture. Consequently, depending upon the circumstances, a "contact product" can be a mixture, a reaction mixture, or a reaction product.

The term "near real-time," as used herein, refers to a delay that is introduced by automated data processing between the occurrence of an event (e.g., live event) and the use of processed data. For example, classifying an event as a near real-time event refers to the delay that allows the use of the processed data near the time of the live event, wherein such delay refers to the difference between the real-time event occurrence and the processing time. Further, such delay can refer to a time interval between when data is received for analysis and when analysis is performed and displayed on an electronic display screen (e.g., monitor screen, computer screen), wherein such time interval can be from less than about 1 minute to less than about 10 minutes, or alternatively from about 3 seconds to about 3 minutes.

The term "real-time" or "actual real-time" as used herein can refer to the instantaneous data processing, wherein a measurement (e.g., measured item, measurement data) is transmitted and received at the same time the measurement is occurring, e.g., data or information is instantaneously or nearly instantaneously streamed or transmitted. For example, the real-time data can be turbidity analysis data or sensor reading data that can be provided instantly (e.g., as soon as it is obtained), such as within about 2 seconds or less from the time the measurement (e.g., a turbidity reading from a turbidimeter) is occurring, to a computer system or computer readable medium.

Although any methods, devices, and materials similar or equivalent to those described herein can be used in the practice or testing of the invention, the typical methods, devices, and materials are herein described.

In an embodiment, a polyethylene production (PEP) system can generally comprise one or more polymerization reactors. In the PEP system embodiments disclosed herein, various system components can be in fluid communication via one or more conduits (e.g., pipes, tubing, or flow lines) suitable for the conveyance of a particular stream, such as for example a reactor feed stream, a reagents stream, or a polymerization catalyst system stream.

In an embodiment, one or more reactor feed streams (e.g., a reagents stream, a polymerization catalyst system stream) can be communicated to a polymerization reactor. In some embodiments, a reagents stream can be purified prior to introducing such stream to the reactor. In one or more of the embodiments disclosed herein, purifying a reagents stream can comprise separating unwanted compounds and elements from a reagents stream comprising ethylene to form a purified feed stream. In an embodiment, purifying a reagents stream can comprise any suitable method or process, including the non-limiting examples of filtering, membrane screening, reacting with various chemicals, absorbing, adsorbing, distillation(s), or combinations thereof.

In an embodiment, a reagents or feed stream can be communicated to a purifier for purification of the reagents stream by removal of one or more undesired compounds therefrom. In an embodiment, the reagents stream can comprise ethylene and various other compounds (in an appropriate physical form such as gases or liquids), such as but not limited to methane, ethane, acetylene, propane, propylene, water, nitrogen, oxygen, various other gaseous hydrocarbons having three or more carbon atoms, various contaminants, or combinations thereof. In one or more of the embodiments disclosed herein, the purifier can comprise a device or apparatus suitable for the purification of one or more reactant gases in a feed stream comprising a plurality of potentially unwanted gaseous compounds, elements, contaminants, and the like. Non-limiting examples of a suitable purifier can comprise a filter, a membrane, a reactor, an absorbent, a molecular sieve, one or more distillation columns, or combinations thereof. The purifier can be configured to separate ethylene from a stream comprising a plurality of potentially unwanted compounds, elements, contaminants, and the like.

In an embodiment, purifying a reagents stream can yield a purified feed stream comprising substantially pure monomers (e.g., substantially pure ethylene). In an embodiment, the purified feed stream can comprise less than about 25% by total weight of the stream, alternatively less than about 10%, alternatively less than about 1.0% of any one or more of nitrogen, oxygen, methane, ethane, propane, comonomers, or combinations thereof. As used herein "substantially pure ethylene" refers to a fluid stream comprising at least about 60% ethylene, alternatively at least about 70% ethylene, alternatively at least about 80% ethylene, alternatively at least about 90% ethylene, alternatively at least about 95% ethylene, alternatively at least about 99% ethylene, or alternatively at least about 99.5% ethylene by total weight of the stream.

In some embodiments, the purified feed stream can comprise a comonomer, such as unsaturated hydrocarbons having from 3 to 20 carbon atoms. Nonlimiting examples of comonomers that can be present in the purified feed stream include alpha olefins, such as for example propylene, 1-butene, 1-pentene, 1-hexene, 3-methyl-1-butene, 4-methyl-1-pentene, 1-heptene, 1-octene, 1-nonene, 1-decene, or combinations thereof.

In an embodiment, the monomers of the purified feed stream can be polymerized in a polymerization reactor to form a polymerization product stream. The polymerization product stream can be formed using any suitable olefin polymerization method which can be carried out using various types of polymerization reactors.

As used herein, the terms "polymerization reactor" or "reactor" include any polymerization reactor capable of polymerizing olefin monomers or comonomers to produce homopolymers or copolymers. Such homopolymers and copolymers are referred to as resins or polymers. The various types of reactors include those that can be referred to as batch, slurry, gas-phase, solution, high pressure, tubular or autoclave reactors. Gas phase reactors can comprise fluidized bed reactors or staged horizontal reactors. Slurry reactors can comprise vertical or horizontal loop reactors. High pressure reactors can comprise autoclave or tubular reactors. Reactor types can include batch or continuous processes. Continuous processes could use intermittent or continuous product discharge. Processes can also include partial or full direct recycle of unreacted monomer, unreacted comonomer, diluent, or combinations thereof. As will be appreciated by one of skill in the art, and with the help of this disclosure, the reactors considered for this disclosure could be any reactors that are part of a polymerization process that employs a polymerization catalyst system comprising at least one solid component.

Polymerization reactor systems of the present disclosure can comprise one type of reactor in a system or multiple reactors of the same or different type. Production of polymers in multiple reactors can include several stages in at least two separate polymerization reactors interconnected by transfer stream(s), line(s), apparatus(es) (for example, a separation vessel(s)), device(s) (for example, a valve or other mechanism), or combinations thereof, making it possible to transfer the polymers resulting from a first polymerization reactor into a second reactor. The desired polymerization conditions in one of the reactors can be different from the operating conditions of the other reactors. Alternatively, polymerization in multiple reactors can include the manual transfer of polymer from one reactor to subsequent reactors for continued polymerization. Multiple reactor systems can include any combination including, but not limited to, multiple loop reactors, multiple gas phase reactors, a combination of loop and gas phase reactors, multiple high pressure reactors or a combination of high pressure with loop reactors, gas phase reactors, or both. The multiple reactors can be operated in series or in parallel.

According to one aspect of this disclosure, the polymerization reactor system can comprise at least one loop slurry reactor comprising vertical or horizontal loops. Monomer, diluent, polymerization catalyst system, and optionally any comonomer can be continuously fed to a loop reactor where polymerization occurs. Generally, continuous processes can comprise the continuous introduction of a monomer, an optional comonomer, a polymerization catalyst system, and a diluent into a polymerization reactor and the continuous removal from this reactor of a suspension comprising polymer particles and the diluent. Reactor effluent can be flashed to remove the solid polymer from the liquids that comprise the diluent, monomer, comonomer, or combinations thereof. Various technologies can be used for this separation step including but not limited to, flashing that can include any combination of heat addition and pressure reduction; separation by cyclonic action in either a cyclone or hydrocyclone; or separation by centrifugation.

A suitable slurry polymerization process (also known as the particle form process), is disclosed, for example, in U.S. Pat. Nos. 3,248,179; 4,501,885; 5,565,175; 5,575,979; 6,239,235; 6,262,191; and 6,833,415; each of which is incorporated by reference herein in its entirety.

In one or more embodiments, suitable diluents used in slurry polymerization include, but are not limited to, the monomer, and optionally the comonomer, being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used.

According to yet another aspect of this disclosure, the polymerization reactor can comprise at least one gas phase reactor. Such systems can employ a continuous recycle stream containing one or more monomers continuously cycled through a fluidized bed in the presence of the catalyst under polymerization conditions. A recycle stream can be withdrawn from the fluidized bed and recycled back into the reactor. Simultaneously, polymer product can be withdrawn from the reactor and new or fresh monomer can be added to replace the polymerized monomer. Likewise, copolymer product can optionally be withdrawn from the reactor and new or fresh comonomer can be added to replace polymerized comonomer, polymerized monomer, or combinations thereof. Such gas phase reactors can comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. Gas phase reactors are disclosed in U.S. Pat. Nos. 5,352,749; 4,588, 790; and 5,436,304; each of which is incorporated by reference herein in its entirety.

According to still another aspect of this disclosure, a high pressure polymerization reactor can comprise a tubular reactor or an autoclave reactor. Tubular reactors, autoclave reactors, or both can have several zones where fresh monomer (optionally, the comonomer), initiators, or a polymerization catalyst system can be added. Monomer (optionally, comonomer) can be entrained in an inert gaseous stream and introduced at one zone of the reactor. Initiators, and polymerization catalyst system components can be entrained in a gaseous stream and introduced at another zone of the reactor. The gas streams can be intermixed for polymerization. Heat and pressure can be employed appropriately to obtain optimal polymerization reaction conditions.

According to still yet another aspect of this disclosure, the polymerization reactor can comprise a solution polymerization reactor wherein the monomer (optionally, comonomer) can be contacted with the polymerization catalyst system by suitable stirring or other means. A carrier comprising an inert organic diluent or excess monomer (optionally, comonomer) can be employed. If desired, the monomer, optional comonomer, or both can be brought in the vapor phase into contact with a catalytic reaction product, in the presence or absence of liquid material. The polymerization zone is maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

Polymerization reactors suitable for the disclosed systems and methods can further comprise at least one raw material feed system, at least one feed system for a polymerization catalyst system or polymerization catalyst system components, at least one polymer recovery system, or combinations thereof. Suitable reactor systems can further comprise systems for feedstock purification, catalyst storage and preparation, extrusion, reactor cooling, polymer recovery, fractionation, recycle, storage, loadout, laboratory analysis, and process control.

Conditions (e.g., polymerization conditions) that are controlled for polymerization efficiency and to provide resin properties include temperature; pressure; type of catalyst or co-catalyst, quantity of catalyst or co-catalyst, or both; and concentrations of various reactants, partial pressures of various reactants, or both.

Polymerization temperature can affect catalyst productivity, polymer molecular weight and molecular weight distribution. Suitable polymerization temperatures can be any temperature below the de-polymerization temperature according to the Gibbs Free energy equation. Typically this includes from about 60° C. (140° F.) to about 280° C. (536° F.), for example, and from about 70° C. (158° F.) to about 110° C. (230° F.), depending upon the type of polymerization reactor.

Suitable pressures will also vary according to the reactor and polymerization type. The pressure for liquid phase polymerizations in a loop reactor is typically less than about 1,000 psig (6.90 MPa). Pressure for gas phase polymerization is usually at about 200 psig (1.38 MPa) to about 500 psig (3.45 MPa). High pressure polymerization in tubular or autoclave reactors is generally run at about 20,000 psig (137.90 MPa) to about 75,000 psig (517 MPa). Polymerization reactors can also be operated in a supercritical region occurring at generally higher temperatures and pressures. Operation above the critical point of a pressure/temperature diagram (supercritical phase) can offer advantages. In an embodiment, polymerization can occur in an environment having a suitable combination of temperature and pressure. For example, polymerization can occur at a pressure in a range of from about 550 psig (3.79 MPa) to about 650 psig (4.48 MPa), or alternatively from about 600 psig (4.14 MPa) to about 625 psig (4.31 MPa) and a temperature in a range of from about 170° F. (77° C.) to about 230° F. (110° C.), or alternatively from about 195° F. (91° C.) to about 220° F. (104° C.).

The concentration of various reactants can be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological parameters.

The concentrations, partial pressures, or both of monomer, comonomer, hydrogen, co-catalyst, modifiers, and electron donors are important in producing these resin properties. Comonomer can be used to control product density. Hydrogen can be used to control product molecular weight. Co-catalysts can be used to alkylate, scavenge poisons and control molecular weight. Modifiers can be used to control product properties and electron donors affect stereoregularity, the molecular weight distribution, molecular weight, or combinations thereof. In addition, the concentration of poisons is minimized because poisons impact the reactions and product properties.

In one or more of the embodiments disclosed herein, monomers in a feed stream (e.g., purified feed stream 11 as illustrated in FIG. 1) can be polymerized. In one or more embodiments, polymerizing monomers of the purified feed stream can comprise allowing a polymerization reaction between a plurality of monomers by contacting a monomer or monomers with a polymerization catalyst system under conditions suitable for the formation of a polymer. In one or more of the embodiments disclosed herein, polymerizing comonomers of the purified feed stream can comprise allowing a polymerization reaction between a plurality of comonomers by contacting a comonomer or comonomers with a polymerization catalyst system under conditions suitable for the formation of a copolymer.

In an embodiment, any suitable polymerization catalyst system can be employed. A suitable polymerization catalyst system can comprise a catalyst; a solid component; and, optionally, a co-catalyst (e.g., organoaluminum compound), a promoter, or both. Nonlimiting examples of polymerization catalyst systems suitable for use in the present disclosure include chromium-based catalysts, chromium oxide catalysts, chromium-silica catalysts, chromium-silica-titania catalysts, chromocene catalysts, metallocene catalysts, Ziegler-Natta catalysts, and the like, or combinations thereof. Catalyst systems suitable for use in the present disclosure have been described, for example, in U.S. Pat. Nos. 7,163,906; 7,619,047; 7,790,820; and 7,960,487, each of which is incorporated by reference herein in its entirety.

In an embodiment, the polymerization catalyst system comprises a solid component comprising a chromium-based catalyst. In an embodiment, the chromium-based catalyst comprises a support material and a chromium compound. In an embodiment, the catalyst comprises chromium (VI).

In an embodiment, the support material of the chromium-based catalyst comprises an inorganic oxide, silica, alumina, silica-alumina, titania, silica-titania, alumina-titania, aluminophosphate, aluminophosphate-titania, magnesia, zirconia, silica-zirconia, alumina-zirconia, ceria (ceric oxide, $CeO_2$), ceria-zirconia (Cr:Zr oxide), boria, thoria (thorium dioxide, $ThO_2$), clay, zeolites, mixed oxides thereof, and the like, or combinations thereof. The support material can be characterized by a surface area and pore volume effective to provide for the production of an active catalyst (e.g., polymerization catalyst).

In an embodiment, the support material has a surface area in the range of from about 10 $m^2$/g to about 1,000 $m^2$/g, alternatively from about 50 $m^2$/g to about 500 $m^2$/g, or alternatively from about 200 $m^2$/g to about 400 $m^2$/g; a pore volume in the range of from about 0.1 cc/g to about 4.0 cc/g, alternatively from about 0.5 cc/g to about 3.5 cc/g, or alternatively from about 0.8 cc/g to about 3.0 cc/g; and an average particle size in the range of from about 5 μm to about 500 μm, alternatively from about 10 μm to about 200 μm, or alternatively from about 25 μm to about 150 μm. Generally, the average pore size of the support material ranges from about 10 Angstroms to about 1,000 Angstroms, alternatively from about 50 Angstroms to about 500 Angstroms, or alternatively from about 75 Angstroms to about 350 Angstroms. The support material can be prepared by using any suitable methodology.

In an embodiment, the support material of the chromium-based catalyst comprises silica. In an embodiment, the support material contains equal to or greater than about 50 wt. % silica, alternatively greater than about 80 wt. % silica, or alternatively greater than about 90 wt. % silica, based on the weight of the support material. In such embodiment, the support material can further comprise additional components that do not adversely affect the catalyst system, such as zirconia, alumina, boria, ceria, thoria, magnesia, fluoride, sulfate, phosphate, and the like, or combinations thereof.

In an embodiment, the support material can comprise silica and the silica support material can be prepared by using any suitable method. For example, the silica support material can be prepared synthetically by hydrolyzing tetrachlorosilane ($SiCl_4$) with water or by contacting sodium silicate with a mineral acid. In an embodiment, the silica support material can have a surface area ranging from about 100 $m^2$/g to about 1,000 $m^2$/g and a pore volume ranging from about 0.1 cc/g to about 2.8 cc/g. In an embodiment, the support material comprises a precipitated silica. For example, the support material can comprise a precipitated or gelled silica. Herein, a gelled or precipitated silica contains a three-dimensional network of primary silica particles.

In another embodiment, the support material of the chromium-based catalyst comprises alumina. The alumina support material can be made using methodologies such as for example: reacting sodium aluminate, which is basic, with aluminum sulfate, which is acidic; neutralizing an aluminum salt with a base such as ammonia or ammonia hydroxide or sodium aluminate; performing flame hydrolysis of an aluminum compound; or performing hydrolysis of an organic solution of an aluminum compound by, e.g., adding water to an alcohol solution of aluminum isopropoxide ($Al(OC_3H_7)_3$). In an embodiment, the alumina support material can have a surface area ranging from about 10 $m^2$/g to about 400 $m^2$/g and a pore volume ranging from about 0.1 cc/g to about 1.8 cc/g.

In yet another embodiment, the support material of the chromium-based catalyst comprises aluminophosphate. The aluminophosphate support material can be prepared by hydrothermal crystallization at elevated temperatures of aluminophosphate gels containing a molecular structure-forming template as described in U.S. Pat. No. 4,310,440, which is incorporated by reference herein in its entirety. Alternatively, the aluminophosphate support material can be made by adding a base to an acidic solution containing $Al^{+3}$ and $PO_4^{-3}$ ions, or alternatively it can be made by treating an alumina or aluminate support with a phosphate source such as phosphoric acid. In an embodiment, the aluminophosphate support material can have a surface area ranging from about 100 $m^2$/g to about 500 $m^2$/g and a pore volume ranging from about 1.0 cc/g to about 2.5 cc/g.

In still another embodiment, the support material of the chromium-based catalyst silica-titania. The silica-titania support material can be made by co-gelation, heterogeneous co-precipitation, or surface impregnation. In an embodiment, the silica-titania support can have a surface area ranging from about 250 m$^2$/g to about 600 m$^2$/g and a pore volume ranging from about 1.0 cc/g to about 3.0 cc/g.

In still yet another embodiment, the support material of the chromium-based catalyst comprises a mixed oxide in which the oxide components can be silica, alumina, aluminophosphate, titania, zirconia, and the like, or combinations thereof, with unique microstructures, varied physical properties, and various methods of making such materials are known to one of skill in the art. Such mixed oxides also have continuous, tightly packed, gel networks which routinely contain unique sheet structures. Furthermore, the mixed oxides are homogeneous (i.e., no individual separate oxide phases are observed), and the pore size, pore size distribution, and volume (meso) of these materials can be tailored.

In some embodiments, the support material comprises a virgin support (e.g., virgin support material). For purposes of the disclosure herein, the term "virgin support" or "virgin support material" refers to a support material that has not been contacted with a polymerization active compound; does not comprise a polymerization active compound; or both. Such virgin support materials can be commercially available compounds that are used "as is" having not undergone any additional treatment following manufacture by a supplier, and thus are in an unadulterated state. Herein, a polymerization active compound refers to a compound or species which can catalyze a polymerization reaction (e.g., polymerization of alpha olefins) or a precursor of such compounds or species. In an embodiment, the virgin support material does not comprise an amount of one or more metals effective to catalyze a polymerization reaction such as olefin polymerization. For example, the virgin support does not include Group VI metals such as Cr, Mo, W, or combinations thereof, in amounts effective to catalyze polymerization reactions. In an embodiment, the virgin support does not comprise chromium or a chromium-containing compound in an amount effective to catalyze a polymerization reaction. In an embodiment, the support material is a virgin support that has not undergone any additional heat treatment since being manufactured, or alternatively has not been previously heated to a temperature of equal to or greater than about 200° C. In an embodiment, the support material comprises virgin silica.

In an embodiment, the support material can be present in the chromium-based catalyst in an amount of from about 90 wt. % to about 99.9 wt. %, alternatively from about 95 wt. % to about 99.5 wt. %, or alternatively from about 98 wt. % to about 99.5 wt. %, based on the total weight of the chromium-based catalyst. In an embodiment, the support material comprises the remainder of the chromium-based catalyst when all other components are accounted for.

In an embodiment, the chromium-based catalyst comprises chromium in the hexavalent oxidation state (hereinafter chromium (VI) or Cr(VI)). In an embodiment, chromium can be introduced to the chromium-based catalyst via contacting one or more of the components of the chromium-based catalyst (e.g., the support material) with a chromium-containing compound. The chromium-containing compound can be one or more compounds comprising Cr(VI) or comprising a material suitable for conversion to Cr(VI). In an embodiment, the chromium-containing compound comprises a water-soluble chromium-containing compound; alternatively the chromium-containing compound comprises a hydrocarbon-soluble chromium compound. The chromium-containing compound can be a chromium (II) compound, a chromium (III) compound, or combinations thereof. Nonlimiting examples of water-soluble chromium compounds suitable for use in the present disclosure include chromium oxide, chromium trioxide, chromium acetate, chromium nitrate, and the like, or combinations thereof. Nonlimiting examples of hydrocarbon-soluble chromium compounds suitable for use in the present disclosure include tertiary butyl chromate, a diarene chromium (0) compound, biscyclopentadienyl chromium(II), chromium (III) acetylacetonate, and the like, or combinations thereof.

In an embodiment, the chromium compound comprises chromium oxide, chromium trioxide, tertiary butyl chromate, a diarene chromium (0) compound, chromium acetates, chromium nitrates, chromium carboxylates, chromium naphthenates, chromium halides, chromium pyrrolides, chromium benzoates, chromium dionates, chromium sulfates, chromium (III) compounds, chromium (III) sulfate, chromium (III) chloride, chromium (III) nitrate, chromic bromide, chromium (III) acetylacetonate, chromium (III) acetate, chromium (III) isooctanoate, chromium (III) 2,2,6,6-tetramethylheptanedionate, chromium (III) naphthenate, chromium (III) tris(2-ethylhexanoate), chromic fluoride, chromium (III) oxy-2-ethylhexanoate, chromium (III) dichloroethylhexanoate, chromium (III) butyrate, chromium (III) neopentanoate, chromium (III) laurate, chromium (III) oxalate, chromium (III) benzoate, chromium (III) pyrrolide(s), chromium (III) perchlorate, chromium (III) chlorate, chromium (II) compounds, chromous fluoride, chromous chloride, chromous bromide, chromous iodide, chromium (II) sulfate, chromium (II) acetate, chromium (II) bis(2-ethylhexanoate), chromium (II) butyrate, chromium (II) neopentanoate, chromium (II) laurate, chromium (II) stearate, chromium (II) oxalate, chromium (II) benzoate, chromium (II) pyrrolide(s), chromous sulfate, biscyclopentadienyl chromium (II), and the like, or combinations thereof.

Nonlimiting examples of chromium compounds suitable for use in the present disclosure include tertiary butyl chromate in a hydrocarbon liquid; chromium trioxide in water; chromium acetate in water; chromium nitrate in alcohol; zerovalent organochromium compounds such as pi bonded chromium complexes, for example, dicumene chromium and dibenzene chromium; and the like; or combinations thereof. Pi bonded chromium complexes are described in U.S. Pat. No. 3,976,632, which is incorporated by reference herein in its entirety.

In an embodiment, chromium can be present in the chromium-based catalyst in an amount of from about 0.1 wt. % to about 10 wt. %, alternatively from about 0.2 wt. % to about 5 wt. %, or alternatively from about 0.5 wt. % to about 2 wt. %, based on the total weight of the chromium-based catalyst. Herein, the wt. % of chromium refers to the final wt. % of chromium associated with the catalyst material by total weight of the material after all processing steps.

In an embodiment, a method of preparing a chromium-based catalyst comprises contacting a support material of the type disclosed herein with a chromium-containing compound of the type disclosed herein to form a chromium-based catalyst. The chromium-containing compound can be introduced to the support material by using any suitable contacting technique. For example, the chromium-containing compound can be contacted with the support material by using techniques such as ion-exchange, incipient wetness impregnation, pore fill, impregnation, and the like, or combinations thereof.

In an embodiment, the dried chromium-based catalyst can be activated to produce an active catalyst (e.g., an active polymerization catalyst). The dried chromium-based catalyst of the present disclosure can be activated using various types of activator equipment. Any vessel or apparatus can be utilized to activate the dried chromium-based catalyst including for example rotary calciners, static pan driers, or fluidized beds. Such equipment can operate in a static, batch, or continuous mode. For the static or batch mode, a vessel or apparatus containing a catalyst bed can be subjected sequentially to various stages of the activation process. For the continuous mode, the stages of the process can occur in a series of zones through which the dried chromium-based catalyst passes on its path through the activation equipment.

In an embodiment, activating the chromium-based catalyst comprises thermal treatment of the chromium-based catalyst. The chromium-based catalyst can be thermally treated (e.g., calcined) by heating in an oxidizing atmosphere to a temperature of less than about 900° C., alternatively from about 300° C. to about 900° C., alternatively from about 400° C. to about 800° C., or alternatively from about 500° C. to about 700° C. for a time period of from about 1 minute to about 24 hours, alternatively from about 30 minutes to about 15 hours, or alternatively from about 1 hour to about 10 hours. In some embodiments, the chromium-based catalyst can be thermally treated in an oxygen-containing atmosphere (e.g., dry air). In such embodiments, the chromium-containing compound (e.g., chromium (III) compound) which was introduced to the chromium-based catalyst by the chromium-containing compound can be oxidized to chromium (VI). In such embodiments, the percentage conversion of Cr(III) to Cr(VI) can range from about 10% to about 100%, alternatively from about 30% to about 90%, or alternatively from about 40% to about 80%.

In an embodiment, the polymerization catalyst system suitable for use in the present disclosure comprises a catalyst comprising at least one metallocene (e.g., metallocene-containing compound). Herein, the term "metallocene" describes a compound comprising at least one $\eta^3$ to $\eta^5$-cycloalkadienyl-type moiety, wherein $\eta^3$ to $\eta^5$-cycloalkadienyl moieties include cyclopentadienyl ligands, indenyl ligands, fluorenyl ligands, and the like, including partially saturated or substituted derivatives or analogs of any of these. Possible substituents on these ligands include hydrogen, therefore the description "substituted derivatives thereof" in this disclosure comprises partially saturated ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like.

In an embodiment, the polymerization catalyst system further comprises a co-catalyst. Generally, a co-catalyst can be employed to activate the catalyst for the polymerization reaction (e.g., polymerization of ethylene to polyethylene). In an embodiment, the co-catalyst can comprise an organoaluminum compound, such as for example an alkylaluminum compound. In an embodiment, the organoaluminum compound can comprise a trialkylaluminum compound, wherein the trialkylaluminum compound can be represented by general formula $AlR_3$.

Nonlimiting examples of trialkylaluminum compounds suitable for use in the present disclosure include triisobutylaluminum (TiBA or TiBAl); tri-n-butylaluminum (TNBA); tri-octyl-butylaluminum (TOBA); triethylaluminum (TEA); trimethylaluminum; diethylaluminum ethoxide; diethylaluminum cyanide; other appropriate alkyl-aluminum complexes, alkylaluminum halides (e.g., diethylaluminum chloride, diisobutylaluminum chloride, ethylaluminum sesquichloride), and the like, or combinations thereof; or combinations thereof. Additionally, partially hydrolyzed alkylaluminum compounds; aluminoxanes (e.g., methylalumoxane (MAO), modified methylalumoxane (MMAO), isobutyl alumoxanes, t-butyl alumoxanes, and the like, or mixtures thereof); or both can be used. In an embodiment, the organoaluminum compound comprises a compound represented by general formula:

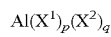

wherein $X^1$ is a halide, hydrocarbyloxide group, hydrocarbylamino group or combinations thereof; $X^2$ is a hydrocarbyl group having up to 18 carbon atoms; p ranges from 0 to 2; and q is (3−p).

In some embodiments, the co-catalyst can comprise organoboron, triethylboron (TEB), organoborate compounds, organolithium compounds, ionizing ionic compounds, and the like, or combinations thereof.

In an embodiment, the polymerization catalyst system comprises a solid component comprising an activator support. The terms "support" and "activator support" are not meant to be construed as an inert component of the catalyst composition (e.g., polymerization catalyst system), but rather are to be considered an active part of the catalyst composition, because of their intimate association with the metallocene component.

In one aspect, the activator support comprises a chemically-treated solid oxide support. Alternatively, the activator support can comprise a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, and the like, or combinations thereof. The terms "chemically-treated solid oxide," "solid oxide activator support," "acidic activator support," "activator support," "treated solid oxide compound," and the like, are used herein to indicate a solid, inorganic oxide of relatively high porosity, which exhibits Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide compound comprises a calcined contact product of at least one solid oxide compound with at least one electron-withdrawing anion source compound. Typically, the chemically-treated solid oxide comprises at least one ionizing, acidic solid oxide compound.

Generally, chemically-treated solid oxides exhibit enhanced acidity as compared to the corresponding untreated solid oxide compounds. The chemically-treated solid oxide can also function as a catalyst activator as compared to the corresponding untreated solid oxide. While the chemically-treated solid oxide activates the metallocene(s) in the absence of co-catalysts, it is not necessary to eliminate co-catalysts from the catalyst composition. The activation function of the activator support is evident in the enhanced activity of catalyst composition as a whole, as compared to a catalyst composition containing the corresponding untreated solid oxide. However, it is believed that the chemically-treated solid oxide can function as an activator, even in the absence of an organoaluminum compound, aluminoxanes, organoboron or organoborate compounds, ionizing ionic compounds, and the like.

In an embodiment, the activator support (e.g., chemically-treated solid oxide) can comprise a solid oxide treated with an electron-withdrawing component (e.g., electron-withdrawing anion). Without wishing to be limited by theory, it is believed that treatment of the solid oxide with an electron-withdrawing component augments or enhances the acidity of the oxide. Thus, either the activator support exhibits Lewis or Brønsted acidity that is typically greater than the Lewis or Brønsted acid strength of the untreated solid oxide, or the activator support has a greater number of acid sites than the untreated solid oxide, or both. One method to quantify the acidity of the chemically-treated and untreated solid oxide materials is by comparing the polymerization activities of the treated and untreated oxides under acid catalyzed reactions.

Chemically-treated solid oxides of this disclosure are formed generally from an inorganic solid oxide that exhibits Lewis acidic or Brønsted acidic behavior and has a relatively high porosity. The solid oxide is chemically-treated with an electron-withdrawing component, typically an electron-withdrawing anion, to form an activator support.

In an embodiment, the solid oxide suitable for use in the present disclosure to prepare the chemically-treated solid oxide can be characterized by a pore volume of greater than about 0.1 cc/g, alternatively greater than about 0.5 cc/g, or alternatively greater than about 1.0 cc/g. In an embodiment, the solid oxide suitable for use in the present disclosure to prepare the chemically-treated solid oxide can be characterized by a surface area of from about 100 m$^2$/g to about 1,000 m$^2$/g, alternatively from about 200 m$^2$/g to about 800 m$^2$/g, or alternatively from about 250 m$^2$/g to about 600 m$^2$/g.

In an embodiment, the chemically-treated solid oxide can comprise a solid inorganic oxide comprising oxygen and one or more elements selected from Group 2, 3, 4, 5, 6, 7, 8, 9, 10, 11, 12, 13, 14, or 15 of the periodic table, or comprising oxygen and one or more elements selected from the lanthanide or actinide elements (See: Hawley's Condensed Chemical Dictionary, 11th Ed., John Wiley & Sons, 1995; Cotton, F. A., Wilkinson, G., Murillo, C. A., and Bochmann, M., Advanced Inorganic Chemistry, 6th Ed., Wiley-Interscience, 1999). For example, the inorganic oxide can comprise oxygen and an element, or elements, selected from Al, B, Be, Bi, Cd, Ce, Co, Cr, Cu, Fe, Ga, La, Mn, Mo, Ni, Sb, Si, Sn, Sr, Th, Ti, V, W, P, Y, Zn, and Zr.

Nonlimiting examples of solid oxides (e.g., solid oxide materials or compounds) that can be used to form the chemically-treated solid oxide suitable for use in the present disclosure include alumina ($Al_2O_3$), boria ($B_2O_3$), BeO, $Bi_2O_3$, ceria ($CeO_2$), CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, silica ($SiO_2$), $SnO_2$, SrO, thoria ($ThO_2$), titania ($TiO_2$), $V_2O_5$, $WO_3$, $Y_2O_3$, zinc oxide (ZnO), zirconia ($ZrO_2$), magnesia (MgO), aluminum phosphate, aluminophosphate, heteropolytungstate, zeolites, silica-alumina, silica-coated alumina, silica-titania, coprecipitated silica/titania, silica-zirconia, alumina-titania, alumina-zirconia, zinc-aluminate, alumina-boria, silica-boria, aluminophosphate-silica, titania-zirconia, and the like, mixed oxides thereof, or combinations thereof. In an aspect of this disclosure, the solid oxide can comprise silica, alumina, silica-alumina, silica-coated alumina, aluminum phosphate, aluminophosphate, heteropolytungstate, titania, zirconia, magnesia, boria, zinc oxide, and the like, mixed oxides thereof, or combinations thereof.

The solid oxide of this disclosure encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound. Nonlimiting examples of mixed oxides suitable for use in the activator support of the present disclosure include silica-alumina, silica-titania, silica-zirconia, zeolites, various clay minerals, alumina-titania, alumina-zirconia, zinc-aluminate, alumina-boria, silica-boria, aluminophosphate-silica, titania-zirconia, and the like, or combinations thereof. The solid oxide of this disclosure also encompasses oxide materials such as silica-coated alumina, as described in U.S. Pat. No. 7,884,163, which is incorporated herein by reference in its entirety.

In an embodiment, the silica-alumina suitable for use in the present disclosure to prepare a chemically-treated silica-alumina can be characterized by a pore volume of greater than about 0.5 cc/g, alternatively greater than about 0.8 cc/g, or alternatively greater than about 1.0 cc/g.

In an embodiment, the silica-alumina suitable for use in the present disclosure to prepare the chemically-treated silica-alumina can be characterized by a surface area of greater than about 100 m$^2$/g to about 1,000 m$^2$/g, alternatively greater than about 250 m$^2$/g, or alternatively greater than about 350 m$^2$/g.

In an embodiment, the silica-alumina suitable for use in the present disclosure to prepare the chemically-treated silica-alumina can be characterized by an alumina content of from about 5 wt. % to about 95 wt. %, based on the total weight of the silica-alumina. In some embodiments, the silica-alumina suitable for use in the present disclosure to prepare the chemically-treated silica-alumina can be characterized by an alumina content of from about 5 wt. % to about 50 wt. %, alternatively from about 8 wt. % to about 30 wt. %, based on the total weight of the silica-alumina. In other embodiments, the silica-alumina suitable for use in the present disclosure to prepare the chemically-treated silica-alumina can be characterized by an alumina content of from about 60 wt. % to about 90 wt. %, alternatively from about 65 wt. % to about 80 wt. %, based on the total weight of the silica-alumina. In yet other embodiments, the solid oxide component can comprise alumina without silica. In still yet other embodiments, the solid oxide component can comprise silica without alumina.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect of the present disclosure, the electron-withdrawing component is an electron-withdrawing anion derived from a salt, an acid, or other compound, such as a volatile organic compound, that serves as a source or precursor for that anion. Nonlimiting examples of electron-withdrawing anions suitable for use in the present disclosure include sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, and the like, or combinations thereof. In addition, other ionic or non-ionic compounds that serve as sources for these electron-withdrawing anions can also be employed in the present disclosure. It is contemplated that the electron-withdrawing anion can be, or can comprise, fluoride, chloride, bromide, phosphate, triflate, bisulfate, or sulfate, and the like, or any combination thereof, in some aspects of this disclosure. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or any combination thereof.

Thus, for example, the activator support (e.g., chemically-treated solid oxide) suitable for use in the polymerization catalyst system of the present disclosure can be, or can comprise, fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, and the like, or combinations thereof. In one aspect, the activator support can be, or can comprise, fluorided alumina, sulfated alumina, fluorided silica-alumina, sulfated silica-alumina, fluorided silica-coated alumina, sulfated silica-coated alumina, phosphated silica-coated alumina, and the like, or any combination thereof. In another aspect, the activator support comprises fluorided alumina; alternatively, comprises chlorided alumina; alternatively, comprises sulfated alumina; alternatively, comprises fluorided silica-alumina; alternatively, comprises sulfated silica-alumina; alternatively, comprises fluorided silica-zirconia; alternatively, comprises chlorided silica-zirconia; or alternatively, comprises fluorided silica-coated alumina. In yet another aspect of the present disclosure, the activator support suitable for use in the catalyst compositions of the present disclosure can be, or can comprise, alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid; and the like; or combinations thereof. Further, any of these activator supports optionally can be treated with a metal ion.

When the electron-withdrawing component comprises a salt of an electron-withdrawing anion, the counterion or cation of that salt can be selected from any cation that allows the salt to revert or decompose back to the acid during calcining. Factors that dictate the suitability of a particular salt to serve as a source for the electron-withdrawing anion include, but are not limited to, the solubility of the salt in a desired solvent, the lack of adverse reactivity of the cation, ion-pairing effects between the cation and anion, hygroscopic properties imparted to the salt by the cation, and the like, and thermal stability of the anion. Nonlimiting examples of cations suitable for use in the present disclosure in the salt of the electron-withdrawing anion include ammonium, trialkyl ammonium, tetraalkyl ammonium, tetraalkyl phosphonium, $H^+$, $[H(OEt_2)_2]^+$, and the like, or combinations thereof.

Further, combinations of one or more different electron-withdrawing anions, in varying proportions, can be used to tailor the specific acidity of the activator support to a desired level. Combinations of electron-withdrawing components can be contacted with the oxide material simultaneously or individually, and in any order that affords the desired chemically-treated solid oxide acidity. For example, one aspect of this disclosure is employing two or more electron-withdrawing anion source compounds in two or more separate contacting steps.

According to another aspect of the present disclosure, the activator support suitable for use in preparing the polymerization catalyst system of this disclosure comprises an ion-exchangeable activator support, including but not limited to silicate and aluminosilicate compounds or minerals, either with layered or non-layered structures, and combinations thereof. In another aspect of this disclosure, ion-exchangeable, layered aluminosilicates such as pillared clays can be used as activator supports. When the acidic activator support comprises an ion-exchangeable activator support, it can optionally be treated with at least one electron-withdrawing anion such as those disclosed previously herein, though typically the ion-exchangeable activator support is not treated with an electron-withdrawing anion.

In an embodiment, the activator support suitable for use in the polymerization catalyst system of this disclosure comprises a clay mineral, dioctahedral (Al) clays, tri-octahedral (Mg) clays, bentonites, montmorillonites, mullites, allophanes, smectites, nontronites, hectorites, laponites, halloysites, vermiculites, micas, fluoromicas, chlorites, mixed-layer clays, fibrous clays, sepiolites, attapulgites, palygorskites, serpentine clays, illites, saponites, a pillared clay, an exfoliated clay, an exfoliated clay gelled into an oxide matrix, a layered silicate mineral, a non-layered silicate mineral, a layered aluminosilicate mineral, a non-layered aluminosilicate mineral, an ion-exchangeable clay, ion-exchangeable layered aluminosilicates, and the like derivatives thereof, or combinations thereof.

According to another aspect of the present disclosure, the activator support suitable for use in the catalyst compositions of the present disclosure can be, or can comprise, a pillared clay, such as a pillared montmorillonite, optionally treated with fluoride, chloride, or sulfate; phosphated alumina or other aluminophosphates optionally treated with sulfate, fluoride, or chloride; or any combination of the above. Further, any of these activator supports optionally can be treated with a metal ion, as previously disclosed herein for the solid oxide activator support.

According to another aspect of the present disclosure, the activator support of this disclosure comprises clay minerals having exchangeable cations and layers capable of expanding. Typical clay mineral activator supports include, but are not limited to, ion-exchangeable, layered aluminosilicates such as pillared clays.

According to yet another aspect of the present disclosure, the clay materials of this disclosure encompass materials either in their natural state or that have been treated with various ions by wetting, ion exchange, or pillaring. Typically, the clay material activator support of this disclosure comprises clays that have been ion exchanged with large cations, including polynuclear, highly charged metal complex cations. However, the clay material activator supports of this disclosure also encompass clays that have been ion exchanged with simple salts, including, but not limited to, salts of Al(III), Fe(II), Fe(III), and Zn(II) with ligands such as halide, acetate, sulfate, nitrate, or nitrite.

According to one aspect of the present disclosure, the activator support comprises a pillared clay. The term "pillared clay" is used to refer to clay materials that have been ion exchanged with large, typically polynuclear, highly charged metal complex cations. Nonlimiting examples of such ions include Keggin ions which can have charges such as 7+, various polyoxometallates, and other large ions. Thus, the term "pillaring" refers to a simple exchange reaction in which the exchangeable cations of a clay material are replaced with large, highly charged ions, such as Keggin ions. These polymeric cations are then immobilized within the interlayers of the clay and when calcined are converted to metal oxide "pillars," effectively supporting the clay layers as column-like structures. Thus, once the clay is dried and calcined to produce the supporting pillars between clay layers, the expanded lattice structure is maintained and the porosity is enhanced. The resulting pores can vary in shape and size as a function of the pillaring material and the parent clay material used. Pillaring and pillared clays are described in more detail in: T. J. Pinnavaia, Science 220 (4595), 365-371 (1983); J. M. Thomas, Intercalation Chemistry, (S. Whittington and A. Jacobson, Eds.) Ch. 3, pp. 55-99, Academic Press, Inc., (1972); U.S. Pat. Nos. 4,452,910; 5,376,611; and 4,060,480; each of which is incorporated herein by reference in its entirety.

The pillaring process utilizes clay minerals having exchangeable cations and layers capable of expanding. Any pillared clay that can enhance the polymerization of olefins in the catalyst composition of the present disclosure can be used. Therefore, suitable clay minerals for pillaring include, but are not limited to, allophanes; smectites, both dioctahedral (Al) and tri-octahedral (Mg) and derivatives thereof such as montmorillonites (bentonites), nontronites, hectorites, or laponites; halloysites; vermiculites; micas; fluoromicas; chlorites; mixed-layer clays; fibrous clays including but not limited to sepiolites, attapulgites, and palygorskites; a serpentine clay; illite; laponite; saponite; and any combination thereof. In one aspect, the pillared clay activator support comprises bentonite or montmorillonite. The principal component of bentonite is montmorillonite.

In some aspects of this disclosure, the pillared clay can be pretreated. For example, a pillared bentonite can be pretreated by drying at about 300° C. under an inert atmosphere, typically dry nitrogen, for about 3 hours, before being added to the polymerization reactor. Although an exemplary pretreatment is described herein, it should be understood that the pretreating can be carried out at many other temperatures and times, including any combination of temperature and time steps, all of which are encompassed by this disclosure.

The activator support used to prepare the catalyst compositions of the present disclosure can be combined with other inorganic support materials, including, but not limited to, zeolites, inorganic oxides, phosphated inorganic oxides, and the like. In one aspect, typical support materials that can be used include, but are not limited to, silica, silica-alumina, alumina, titania, zirconia, magnesia, boria, ceria, thoria, aluminophosphate, aluminum phosphate, silica-titania, coprecipitated silica/titania, mixtures thereof, or any combination thereof.

In an embodiment, a process of making activator supports comprising inorganic support materials can include precipitation, co-precipitation, impregnation, gelation, pore-gelation, calcining (at up to about 900° C.), spray-drying, flash-drying, rotary drying and calcining, milling, sieving, or combinations thereof.

In an embodiment, the activator support suitable for use in the present disclosure can be characterized by an average particle size of average particle size of from about 5 µm to about 500 µm, alternatively from about 10 µm to about 250 µm, or alternatively from about 25 µm to about 200 µm.

In an aspect of this disclosure polymerizing monomers of the purified feed stream to form a polymerization product stream can be carried out using a loop slurry process, such as for example a loop slurry process 100 illustrated in the embodiment of FIG. 1. The loop slurry process 100 generally comprises a purifier 102, a turbidimeter 103, and a first reactor 104. The loop slurry process 100 can optionally comprise a second reactor 106. In the loop slurry process embodiments disclosed herein, various system components can be in fluid communication via one or more conduits (e.g., pipes, tubing, or flow lines) suitable for the conveyance of a particular stream, for example as shown in detail by the numbered streams in FIG. 1.

In an embodiment, a reagent stream 10 can be communicated to a purifier 102, and a purified feed stream 11 can be communicated from the purifier 102 to one or more of the reactors (e.g., a first reactor 104, a second reactor 106). Where the loop slurry process comprises two or more reactors, a mid-polymerization reactor stream 15 can be communicated from the first reactor 104 to the second reactor 106. A polymerization product stream 121 can be emitted from the first reactor 104, the second reactor 106, or both. Hydrogen (not shown) can be introduced to the first reactor 104, to the second reactor 106, or both in stream 21.

In embodiments as illustrated by FIG. 1, polymerizing monomers of the purified feed stream can comprise routing the purified feed stream 11 to the one or more of the polymerization reactors 104, 106. Polymerizing monomers of the mid-polymerization reactor stream 15 can comprise routing the mid-polymerization reactor stream 15 to polymerization reactor(s) 106. In embodiments as illustrated by FIG. 1, polymerizing monomers of the mid-polymerization reactor stream 15 can comprise routing the mid-polymerization reactor stream 15 from polymerization reactor(s) 104 to polymerization reactor(s) 106.

In one or more of the embodiments disclosed herein, the polymerization reactors 104, 106 can comprise any vessel or combination of vessels suitably configured to provide an environment for a chemical reaction (e.g., a contact zone) between monomers (e.g., ethylene), polymers (e.g., an "active" or growing polymer chain), or both; and optionally comonomers, copolymers, or both, in the presence of a catalyst to yield a polymer (e.g., a polyethylene polymer), a copolymer, or both. Although the embodiments illustrated in FIG. 1 illustrate a PEP system having two reactors in series, one of skill in the art viewing this disclosure will recognize that one reactor, alternatively, any suitable number of reactors, configuration of reactors, or both can be employed.

In embodiments as illustrated in FIG. 1, production of polymers in multiple reactors can include at least two polymerization reactors 104, 106 interconnected by one or more devices or apparatus (e.g., valve, continuous take-off valve, continuous take-off mechanism, or combinations thereof). In embodiments as illustrated in FIG. 1, production of polymers in multiple reactors can include at least two polymerization reactors 104, 106 interconnected by one or more streams or lines (e.g., mid-polymerization reactor stream 15). In some embodiments, production of polymers in multiple reactors can include at least two polymerization reactors 104, 106 interconnected by one or more separators (e.g., flash chambers).

In an embodiment, polymerizing monomers can comprise introducing a suitable polymerization catalyst system into the first reactor 104, the second reactor 106, or both, so as to form a slurry. For example, a polymerization catalyst system can be communicated to one or more of the reactors (e.g., a first reactor 104, a second reactor 106) via a reactor feed stream 12a. At least a portion of a reactor feed stream 12 (e.g., a polymerization catalyst system stream) can be communicated to a turbidimeter 103 to measure the turbidity of the stream, as will be described in more detail later herein. A reactor feed stream 12a can be communicated from the turbidimeter 103 to one or more of the reactors (e.g., a first reactor 104, a second reactor 106).

As previously described herein, polymerizing monomers can comprise selectively manipulating one or more polymerization reaction conditions to yield a given polymer product, to yield a polymer product having one or more desirable properties, to achieve a desired efficiency, to achieve a desired yield, the like, or combinations thereof. In an embodiment, polymerizing monomers of the purified feed stream 11 can comprise adjusting one or more polymerization reaction conditions.

In an embodiment, polymerizing monomers can comprise maintaining a suitable temperature, pressure, partial pressure(s), or combinations thereof during the polymerization reaction; alternatively, cycling between a series of suitable temperatures, pressures, partial pressure(s), or combinations thereof during the polymerization reaction.

In an embodiment, polymerizing monomers can comprise polymerizing comonomers in one or more of polymerization reactors 104, 106. In an embodiment, polymerizing monomers can comprise introducing ethylene monomer, a comonomer, or both to the polymerization reactor 106.

In an embodiment, polymerizing monomers can comprise circulating, flowing, cycling, mixing, agitating, or combinations thereof, the monomers (optionally, comonomers), the polymerization catalyst system, the slurry, or combinations thereof, within the reactors 104, 106, between the reactors 104, 106, or both. In an embodiment where the monomers (optionally, comonomers), polymerization catalyst system, slurry, or combinations thereof, are circulated, circulation can be at a velocity (e.g., slurry velocity) of from about 1 m/s to about 30 m/s, alternatively from about 2 m/s to about 17 m/s, or alternatively from about 3 m/s to about 15 m/s.

In the embodiments illustrated in FIG. 1, polymerizing monomers of the purified feed stream 11 can yield polymerization product stream 121. In an embodiment, the polymerization product stream 121 can generally comprise various solids, semi-solids, volatile and nonvolatile liquids, gases and combinations thereof. Polymerizing monomers of the purified feed stream 11 can yield the polymerization product stream 121 generally comprising unreacted monomer (e.g., ethylene), optional unreacted comonomer, by-products (e.g., ethane, which can be by-product ethane formed from ethylene and hydrogen), and a polymerization product (e.g., polymer and optionally, copolymer). As used herein, an "unreacted monomer," for example, ethylene, refers to a monomer that was introduced into a polymerization reactor during a polymerization reaction but was not incorporated into a polymer. As used herein, an "unreacted comonomer" refers to a comonomer that was introduced into a polymerization reactor during a polymerization reaction but was not incorporated into a polymer. The gases of the polymerization product stream 121 can comprise unreacted, gaseous reactant monomers or optional comonomers (e.g., unreacted ethylene monomers, unreacted comonomers), gaseous waste products, gaseous contaminants, or combinations thereof. The solids of the polymerization product stream 121, the liquids of the polymerization product stream 121, or both can comprise a polymer product (e.g., a polyethylene polymer), often referred to at this stage of the PEP process as "polymer fluff."

In an embodiment, the polymerization product stream can be further processed (e.g., by flashing or purging) to remove gases and liquids and to obtain a polymer stream. In one or more of the embodiments disclosed herein, the polymer stream can be further processed, wherein processing the polymer stream comprises any suitable process or series of processes configured to produce a polymer product as can be suitable for commercial or industrial usage, storage, transportation, further processing, or combinations thereof.

In an embodiment, a method of monitoring a solid component of a reactor feed stream in a polymer production system (e.g., polyethylene production system) can generally comprise the step of measuring a turbidity of the reactor feed stream, wherein the reactor feed stream comprises a solid component of a polymerization catalyst system.

In an embodiment, measuring the turbidity of the reactor feed stream can comprise passing at least a portion of the feed stream (e.g., polymerization catalysts system stream, reactor feed stream 12) through a turbidimeter (e.g., turbidimeter 103), and obtaining an output signal representing turbidity from the turbidimeter.

Generally, a turbidimeter is an analytical instrument that measures turbidity of fluids by measuring a loss of intensity of transmitted light due to the light scattering effect, light absorbing effect, or both of particles suspended in the fluid. A light beam (e.g., incident light beam) of a known wavelength can be passed through a measuring cell (e.g., a flow cell, or a cuvette) containing a fluid with suspended solid particles (e.g., a polymerization catalyst system stream comprising a solid component). The presence of solid particles (e.g., solid component of a polymerization catalyst system) in the fluid causes the light to be scattered and absorbed rather than transmitted straight through the sample. The extent of light scattering and absorption is dependent on the solid particles properties, such as for example particle composition, particle shape, particle size, particle color, refractive index of the particle. A measuring device (e.g., photodetector, photoelectric cell, photomultiplier tube, vacuum photodiode, silicon photodiode, cadmium sulfide photoconductor) measures the light that passes through the measuring cell. The measuring device can be aligned with the incident light beam, or it can be placed at an angle with the incident light beam (e.g., a 90° angle with the incident light beam). The turbidimeter relays a signal (e.g., turbidity) that accounts for the attenuation of light intensity passing through the measuring cell, and such signal correlates to an amount (e.g., concentration) of solid particles (e.g., solid component of a polymerization catalyst system) present in the fluid. In some instances, the fluid can absorb at the wavelength of the incident light beam, and in such case the fluid provides for a background signal that has to be subtracted from the measured turbidity. For example, the fluid can comprise solubilized components (e.g., a catalyst such as metallocene that is soluble in the polymerization catalyst system stream), wherein such solubilized components can absorb at the wavelength of the incident light beam.

In some embodiments, a portion of the reactor feed stream can be routed from the feed stream through a turbidimeter (e.g., through a measuring flow cell of a turbidimeter) to measure the turbidity of the feed stream. Upon measuring the turbidity, the portion of the reactor feed stream that was routed from the feed stream through the turbidimeter can be returned to the reactor feed stream and can be communicated to the reactor (e.g., a polymerization reactor, a loop slurry reactor, a gas phase reactor) as part of the feed stream. Alternatively, the portion of the reactor feed stream that was routed from the feed stream through the turbidimeter can be communicated to the reactor without mixing with the reactor feed stream that it was removed from prior to the turbidity measurement.

In other embodiments, the entire reactor feed stream (as opposed to just a portion of the reactor feed stream) can be routed through a turbidimeter (e.g., through a measuring flow cell of a turbidimeter) to measure the turbidity of the feed stream. Upon measuring the turbidity, the reactor feed stream can be communicated to the reactor (e.g., a polymerization reactor, a loop slurry reactor, or a gas phase reactor).

In other embodiments, the reactor feed stream (e.g., reactor feed stream 12) can be communicated to a turbidimeter (e.g., through a measuring flow cell of a turbidimeter 103) to measure the turbidity of the feed stream. Upon measuring the turbidity of the feed stream, the turbidimeter can communicate the reactor feed stream (e.g., reactor feed stream 12a) to the reactor.

As will be appreciated by one of skill in the art, and with the help of this disclosure, the reactor feed stream 12 and the reactor feed stream 12a have the same turbidity. The reactor feed stream 12 and the reactor feed stream 12a are essentially the same stream, wherein reactor feed stream 12 is the reactor feed stream prior to the turbidity measurement, and wherein reactor feed stream 12a is the reactor feed stream subsequent to the turbidity measurement.

In an embodiment, the reactor feed stream comprises a polymerization catalyst system comprising a solid component. In an embodiment, the reactor feed stream can comprise a carrier fluid, wherein the carrier fluid helps convey (e.g., communicate, transport) one or more components of the polymerization catalyst system to a reactor via a reactor feed stream. Nonlimiting examples of carrier fluids suitable for use in the present disclosure include hydrocarbons, propane, cyclohexane, isobutane, n-butane, n-pentane, isopentane, neopentane, n-hexane, n-heptane, and the like, or combinations thereof. In an embodiment, the carrier fluid comprises isobutane.

In an embodiment, a method of monitoring a solid component of a reactor feed stream in a polymer production system (e.g., polyethylene production system) can generally comprise the step of translating the turbidity of the reactor feed stream into a concentration of the solid component in the reactor feed stream.

In an embodiment, translating the turbidity of the reactor feed stream into a concentration of the solid component in the reactor feed stream comprises using a calibration curve with known solid component concentration values as a function of measured turbidity. A calibration curve with known solid component concentration values as a function of measured turbidity can be obtained by preparing slurry solutions with known concentrations of the solid component in the carrier fluid, measuring the turbidity of the slurry solutions, and plotting the known concentrations of the solid component in the carrier fluid as a function of the corresponding measured turbidity. As will be appreciated by one of skill in the art, and with the help of this disclosure, while as little as two measurements can be used for drawing a calibration curve, at least three values should be used for constructing the calibration curve, preferably as many values as it is deemed to be statistically significant for any particular case.

As will be appreciated by one of skill in the art, and with the help of this disclosure, a calibration curve is generally accompanied by a mathematical equation describing the calibration curve, and the mathematical equation can be used as well for translating the turbidity of the reactor feed stream into a concentration of the solid component by plugging into the equation the measured turbidity value and calculating the corresponding concentration.

Further, as will be appreciated by one of skill in the art, and with the help of this disclosure, sometimes the turbidimeters could have an inherent systematic bias, and as such it can be preferable to construct the calibration curve with the same turbidimeter which is used for measuring the turbidity of the reactor feed stream and with the same light source at the same wavelength of incident light.

In an embodiment, translating the turbidity of the reactor feed stream into a concentration of the solid component in the reactor feed stream can further comprise subtracting a background signal from the measured turbidity of the reactor feed stream. Generally, the carrier fluid does not create a background signal. However, certain polymerization catalysts system components (e.g., activator; or catalyst, such as metallocene, chromium-based catalyst, or Ziegler-Natta catalyst) can be at least partially solubilized (e.g., dissolved) in the carrier fluid, can absorb light at the wavelength of incident light, or both; and as such would contribute to the measured turbidity signal. In such instances, the turbidimeter can be used for measuring a background signal of the carrier fluid comprising the dissolved component that absorbs light at the wavelength of incident light in the absence of the solid component, and the background signal can be subtracted from the measured turbidity. As will be appreciated by one of skill in the art, and with the help of this disclosure, the background signal will be dependent on the concentration in the carrier fluid of the dissolved component that absorbs light at the wavelength of incident light.

In some embodiments, the polymerization catalyst system (e.g., a chromium-based catalyst, a metallocene-type catalyst, or a Ziegler-Natta catalyst) can be prepared and communicated to the reactor via a reactor feed stream, wherein the turbidity of the reactor feed stream can be measured with a turbidimeter located prior to the feed stream entering the reactor.

In other embodiments, components of the polymerization catalyst system can be mixed with each other at different locations within the PEP system. For example, the solid component of the polymerization catalyst system (e.g., activator support of a metallocene-based catalyst system) can be mixed with a carrier fluid and stored in a storage tank upstream of the reactor. In such embodiment, the turbidity of the reactor feed stream can be measured downstream of the storage tank. As will be appreciated by one of skill in the art, and with the help of this disclosure, the solid component can be mixed with the carrier fluid for facilitating dispensing known amounts of the solid component, for facilitating communicating the solid component to the reactor, or both. In an embodiment, the turbidity of the reactor feed stream can be measured downstream of the storage tank and upstream of the reactor.

In an embodiment, a mass balance can be calculated across the storage tank to yield an amount of the solid component in the storage tank. When the turbidimeter is located downstream of the storage tank, it should be theoretically known what amount of solid component is being dispensed over a given time frame from the storage tank. Also, provided that the amount of solid component that is introduced to the storage tank over the same time frame is known as well, it can be calculated how much solid component is present in the storage tank. Alternatively, the turbidimeter can help calculate the amount of solid component that was dispensed over a given time frame from the storage tank (e.g., by using the turbidity of a storage tank effluent stream such as a reactor stream, and a flow rate of such stream), and the calculated amount of dispensed solid component can be used to calculate how much solid component is present in the storage tank. As will be appreciated by one of skill in the art, and with the help of this disclosure, the turbidimeter might either overestimate or underestimate the amount of solid component that was dispensed over a given time frame from the storage tank, thereby respectively underestimating or overestimating the amount of solid component present in the storage tank. In the case when the calculated amount (e.g., calculated from the turbidity signal) of solid component that was dispensed over a given time frame from the storage tank is different from the actual amount of solid component that was dispensed over the same time frame from the storage tank, a correlation factor between the calculated amount of dispensed solid component and the actual amount of dispensed solid component can be calculated. For example, a correlation factor could be calculated by dividing the calculated amount of dispensed solid component by the actual amount of dispensed solid component, or by dividing the actual amount of dispensed solid component by the calculated amount of dispensed solid component.

In an embodiment, a mass balance can be calculated across the storage tank to yield a correlation factor, wherein the correlation factor can be used with the calibration curve (e.g., calibration curve with known solid component concentration values as a function of measured turbidity) for translating the turbidity of the reactor feed stream into a concentration of the solid component in the reactor feed stream. As will be appreciated by one of skill in the art, and with the help of this disclosure, the correlation factor serves as a correction factor between the concentration of the solid component calculated from turbidity data and the actual concentration of the solid component.

In an embodiment, the turbidimeter can provide near real-time data or information about the storage tank running empty. In an embodiment, measuring the turbidity of the reactor feed stream downstream of the storage tank can provide near real-time data about the storage tank running empty. As will be appreciated by one of skill in the art, and with the help of this disclosure, a slight delay can be introduced by automated data processing, between measuring the turbidity and using of processed data, thereby rendering such data as near real-time data. Further, as will be appreciated by one of skill in the art, and with the help of this disclosure, when the storage tank runs empty, the stream analyzed by the turbidimeter contains no solid component, and as such the turbidity signal goes to zero or to a background signal level it has in the absence of the solid component. In some embodiments, the turbidity signal can surge (e.g., sharply increase) immediately prior to the turbidity signal going to zero or to a background signal level it has in the absence of the solid component.

In an embodiment, the turbidity (e.g., turbidity signal) can vary when a storage tank pressure varies. The varying pressure in the storage tank can possibly result in a varied feed rate of the solid component of the polymerization catalyst system. In some embodiments, a pressure decrease in the storage tank can result in a lower turbidity signal and a lower feed rate of the solid component of the polymerization catalyst system. In other embodiments, a pressure increase in the storage tank can result in a higher turbidity signal and a higher feed rate of the solid component of the polymerization catalyst system. As will be appreciated by one of skill in the art, and with the help of this disclosure, a decrease in turbidity signal can provide near real-time information as to an unexpectedly low feed rate of the solid component of the polymerization catalyst system to the reactor. Further, as will be appreciated by one of skill in the art, and with the help of this disclosure, pressure ranges can vary depending on design pressures in each individual plant: the low end of the pressure range is usually the pressure of a reactor feed line or the reactor itself, and the upper end of the pressure range is the upper design pressure of the storage tank. Storage tank pressure increases and decreases can occur by different means. Further, as will be appreciated by one of skill in the art, and with the help of this disclosure, when using a fixed volume metering device (e.g., a ball check feeder) downstream of the storage tank, a pressure variance in the storage tank will have an effect (i.e., increase or decrease) on the fill efficiency of that fixed volume metering device; the extent of such effect is related to the magnitude of the pressure change, as well as to the properties of the particular solid support (e.g., solid component of the polymerization catalyst system) being used. Generally, a higher fill efficiency will lead to an underestimation of the solid component of the polymerization catalyst system, and a lower fill efficiency will lead to an overestimation of the solid component of the polymerization catalyst system. Further, a similar situation can be encountered if the discharge pressure of a pump on a solid-liquid slurry tank varies from set-point and results in a corresponding variance in feed rate and turbidity signal of the solid component of the polymerization catalyst system.

In an embodiment, the turbidimeter can be located downstream of a solid component delivery device. In such embodiment, the solid component delivery device can be located downstream of the storage tank, wherein the solid component delivery device can be used for dispensing the solid component from the storage tank. In an embodiment, the turbidity of the reactor feed stream can be measured downstream of the solid component delivery device and upstream of the reactor.

In some embodiments, the solid component delivery device provides for intermittent delivery of the solid component into the reactor feed stream. In such embodiments, the solid component delivery device comprises a fixed-volume metering device, a rotary ball check feeder, and the like, or combinations thereof.

In other embodiments, the solid component delivery device provides for continuous delivery of the solid component into the reactor feed stream. In such embodiments, the solid component delivery device comprises a pump suitable for delivery of the solid component, a device for measuring a delivery rate of the solid component, and the like, or combinations thereof.

In an embodiment, the turbidity of the reactor feed stream, the concentration of the solid component in the reactor feed stream, or both can be averaged over a time period to yield an averaged turbidity, an averaged concentration, or both. In such embodiment, the time period can be less than about 4 hours, alternatively less than about 3 hours, alternatively less than about 2 hours, alternatively less than about 1 hour, alternatively less than about 30 minutes, alternatively less than about 15 minutes, alternatively less than about 5 minutes, alternatively less than about 1 minute, alternatively less than about 30 seconds, alternatively less than about 10 seconds, alternatively from about 10 seconds to about 4 hours, alternatively from about 1 minute to about 3 hours, alternatively from about 15 minutes to about 2 hours, or alternatively from about 30 minutes to about 90 minutes.

In an embodiment, the time period can be a residence time of the solid component in a reactor. Generally the residence time of a solid component in a vessel (e.g., a reactor, a precontactor) refers to the average amount of time that a particle of the solid component spends in that particular container. When the solid component of the polymerization catalyst system has a known residence time in the reactor, the turbidity of the reactor feed stream, the concentration of the solid component in the reactor feed stream, or both can be averaged over that particular residence time to allow for calculating the amount of the solid component of the polymerization catalyst system in the reactor, such as for example via a mass balance across the reactor.

In an embodiment, the polymerization catalyst system comprises a chromium-based catalyst, wherein the chromium-based catalyst is characterized by a reactor residence time of from about 30 minutes to about 90 minutes, alternatively from about 45 minutes to about 75 minutes, or alternatively from about 50 minutes to about 70 minutes. In such embodiment, the turbidity of the reactor feed stream, the concentration of the chromium-based catalyst in the reactor feed stream, or both can be averaged over the reactor residence time to yield an averaged turbidity of the rector feed stream, an averaged concentration of the chromium-based catalyst in the reactor feed stream, or both.

In an embodiment, the polyethylene production system can comprise a precontactor, wherein the precontactor can be configured to receive at least a portion of two or more components of the polymerization catalyst system. In such embodiment, at least one of the two or more components of the polymerization catalyst system comprises the solid component. The precontactor is located upstream of the reactor.

In some embodiments, two or more components of the polymerization catalyst system can contact each other upstream of the precontactor. In such embodiments, the two or more components of the polymerization catalyst system that contact each other upstream of the precontactor can form a precontactor feed stream, wherein the precontactor feed stream can be communicated to the precontactor. In an embodiment, the precontactor feed stream comprises a reactor feed stream.

In an embodiment, the precontactor can be characterized by a residence time of the solid component in the precontactor. In such embodiment, the residence time of the solid component in the precontactor can be from about 1 minute to about 120 minutes, alternatively from about 10 minutes to about 90 minutes, or alternatively from about 20 minutes to about 60 minutes.

In an embodiment, the turbidity of a reactor feed stream can be measured upstream of the precontactor, downstream of the precontactor, or both, wherein the turbidimeter is located upstream of the reactor. In an embodiment, the precontactor can be located downstream of a storage tank and upstream of the reactor.

In an embodiment, the turbidity of the reactor feed stream, the concentration of the solid component in the reactor feed stream, or both can be averaged over the residence time of the solid component in the precontactor. In an embodiment, a mass balance can be calculated across the precontactor to yield an amount of solid component in the precontactor. When the solid component of the polymerization catalyst system has a known residence time in the precontactor, the turbidity of the precontactor feed stream, the concentration of the solid component in the precontactor feed stream, or both can be averaged over that particular residence time to allow for calculating the amount of the solid component of the polymerization catalyst system in the precontactor, such as for example via a mass balance across the precontactor.

In an embodiment, the turbidimeter can be located upstream of the precontactor. In such embodiment, the turbidity of the reactor feed stream, the concentration of the solid component in the reactor feed stream, or both can be averaged over the residence time of the solid component in the precontactor.

In an embodiment, the solid component of the polymerization catalyst system comprises the activator support, wherein the polymerization catalyst system can be a metallocene-based catalyst system. In such embodiment, the activator support can be fed to a precontactor, wherein the precontactor can be configured to receive the polymerization catalyst system via one or more precontactor feed streams, and wherein at least one of the precontactor feed streams comprises at least a portion of the activator support.

In an embodiment, at least one of the precontactor feed streams comprises at least a portion of the activator support and a carrier fluid. In an embodiment, the reactor feed stream comprises at least a portion of a precontactor feed stream comprising at least a portion of the activator support.

In an embodiment, at least one of the precontactor feed streams comprises at least a portion of a catalyst (e.g., at least one metallocene), at least a portion of a co-catalyst (e.g., organoaluminum compound), or both. The catalyst and the co-catalyst can be solubilized in a carrier fluid.

In an embodiment, at least a portion of a catalyst and at least a portion of a co-catalyst can contact each other upstream of the precontactor.

In some embodiments, a first precontactor feed stream comprises at least a portion of a catalyst solubilized in carrier fluid, and a second precontactor feed stream comprises at least a portion of a co-catalyst solubilized in carrier fluid, wherein the carrier fluid used for solubilizing each of the catalyst and co-catalyst can be the same or different. In such embodiments, at least a portion of the first precontactor feed stream and at least a portion of the second precontactor feed stream can each be communicated individually (e.g., separately, independently from each other) to the precontactor.

In other embodiments, at least a portion of the first precontactor feed stream comprising a catalyst solubilized in carrier fluid, and at least a portion of the second precontactor feed stream comprising a co-catalyst solubilized in carrier fluid can contact each other upstream of the precontactor to form a common precontactor feed stream comprising both a catalyst and a co-catalyst, wherein the carrier fluid used for solubilizing each of the catalyst and co-catalyst can be the same or different. In such embodiments, at least a portion of the common precontactor feed stream comprising both a catalyst and a co-catalyst can be communicated to the precontactor.

In yet other embodiments, at least one of the precontactor feed streams comprises at least a portion of two or more components of the polymerization catalyst system, wherein the components of the polymerization catalyst system can be selected from the group consisting of activator support, catalyst (e.g., at least one metallocene) and co-catalyst (e.g., organoaluminum compound). In such embodiments, at least a portion of individual precontactor feed streams can be combined upstream of the precontactor, or alternatively can be combined in the precontactor.

In an embodiment, the activator support can be characterized by a precontactor residence time of from about 1 minute to about 60 minutes, alternatively from about 5 minutes to about 30 minutes, or alternatively from about 10 minutes to about 15 minutes.

In an embodiment, a turbidity of a precontactor feed stream comprising at least a portion of the activator support can be averaged over the precontactor residence time to yield an averaged turbidity of the activator support, an averaged concentration of the activator support, or both. In an embodiment, a mass balance can be calculated across the precontactor to yield an amount of activator support in the precontactor. When the activator support has a known residence time in the precontactor, the turbidity of the precontactor feed stream, the concentration of the solid component in the precontactor feed stream, or both can be averaged over that particular residence time to allow for calculating the amount of the activator support in the precontactor, such as for example via a mass balance across the precontactor.

In an embodiment, the activator support can be stored in a storage tank upstream of a reactor. In such embodiment, the turbidity of the reactor feed stream can be measured downstream of the storage tank and upstream of the reactor.

In an embodiment, a mass balance can be calculated across the storage tank to yield an amount of the activator support in the storage tank. When the turbidimeter is located downstream of the storage tank, it should be theoretically known what amount of activator support is being dispensed over a given time frame from the storage tank. Also, provided that the amount of activator support that is introduced to the storage tank over the same time frame is known as well, it can be calculated how much activator support is present in the storage tank. Alternatively, the turbidimeter can help calculate the amount of activator support that was dispensed over a given time frame from the storage tank (e.g., by using the turbidity of a storage tank effluent stream such as a reactor stream, and a flow rate of such stream), and the calculated amount of dispensed activator support can be used to calculate how much activator support is present in the storage tank. In the case when the calculated amount (e.g., calculated from the turbidity signal) of activator support that was dispensed over a given time frame from the storage tank is different from the actual amount of activator support that was dispensed over the same time frame from the storage tank, a correlation factor between the calculated amount of dispensed activator support and the actual amount of dispensed activator support can be calculated. For example, a correlation factor could be calculated by dividing the calculated amount of dispensed activator support by the actual amount of dispensed activator support, or by dividing the actual amount of dispensed activator support by the calculated amount of dispensed activator support.

In an embodiment, a mass balance can be calculated across the storage tank to yield a correlation factor, wherein the correlation factor can be used with the calibration curve (e.g., calibration curve with known activator support concentration values as a function of measured turbidity) for translating the turbidity of the reactor feed stream into a concentration of the activator support in the reactor feed stream.

In an embodiment, the storage tank can be located upstream of a precontactor. In such embodiment, the turbidity of the reactor feed stream can be measured (i) downstream of the storage tank and upstream of the precontactor; (ii) downstream of the precontactor and upstream of the reactor; or combinations thereof.

In an embodiment, the concentration of the solid component in the reactor feed stream can be used for calculating one or more ratios of components of the polymerization catalyst system, wherein the concentration of the solid component was calculated by using turbidimeter measurements as disclosed herein. In such embodiment, the one or more ratios of components of the polymerization catalyst system can be compared to one or more target ratios. The target ratios of components of the polymerization catalyst system will vary according to the desired polymerization reaction product. As will be appreciated by one of skill in the art, and with the help of this disclosure, the target ratios of components of the polymerization catalyst system can be set based on a desired outcome of the polymerization reaction, i.e., based on the desired properties for the final polymer product, such as for example molecular weight, density, modality.

In some embodiments, the one or more ratios of components of the polymerization catalyst system are the same when compared to the one or more target ratios.

In other embodiments, the one or more ratios of components of the polymerization catalyst system are different when compared to the one or more target ratios. In such embodiments, an amount of at least one component of the polymerization catalyst system can be adjusted to meet the target ratios.

In an embodiment, the polyethylene production system can further comprise a control system, wherein the control system comprises at least one processor (e.g., computer) and at least one controller (e.g., actuator). Generally, a control system is a device, or set of devices (e.g., at least one processor and at least one controller) that manages, commands, directs or regulates the behavior of other devices or systems (e.g., polyethylene production equipment or machines, such as a device for dispensing a polymerization catalyst system component).

In an embodiment, the control system can be a distributed control system (DCS). Generally, a DCS is a control system for a process (e.g., polyethylene production process) or plant (e.g., polyethylene production plant), wherein control elements are distributed throughout the control system (as opposed to non-distributed control systems, which use a single controller at a central location). DCS controllers can be connected by communications networks for command and monitoring.

In an embodiment, the at least one processor can receive from at least one turbidimeter a turbidity signal representing the turbidity of a stream (e.g., reactor feed stream, precontactor feed stream, or precontactor effluent stream). In such embodiment, the at least one processor can translate the turbidity signal into a concentration of the solid component in the stream, for example by using a calibration curve with known solid component concentration values as a function of measured turbidity.

In an embodiment, the at least one processor of the control system can calculate one or more ratios of components of the polymerization catalyst system using the concentration of the solid component in the reactor feed stream. The processor receives information/data about components of the polymerization catalyst system other than the solid component as well, and the processor can utilize such data for calculating one or more ratios of components of the polymerization catalyst system. For example, in a metallocene-based catalyst system, a concentration of a metallocene (e.g., catalyst) in a stream can be determined by using ultraviolet-visible (UV-Vis) spectroscopy, and the concentration of an organoaluminum compound (e.g., co-catalyst) in a stream can be determined by calculation from a known concentration of the organoaluminum compound in a feed stream.

In an embodiment, the at least one processor of the control system can compare the one or more ratios of components of the polymerization catalyst system to one or more target ratios.

In some embodiments, the one or more ratios of components of the polymerization catalyst system are the same when compared to the one or more target ratios, and the processor does not require further action for correcting the one or more ratios of components of the polymerization catalyst system.

In other embodiments, the one or more ratios of components of the polymerization catalyst system are different when compared to the one or more target ratios. In such embodiments, the at least one processor can signal the at least one controller and directs the at least one controller to correct the one or more ratios of components of the polymerization catalyst system by adjusting an amount of at least one component of the polymerization catalyst system to meet the target ratios. For example, the at least one controller can be an actuator that controls a valve (e.g., a feeder valve, or a rotary ball check feeder) and allows for dispensing a specific amount of a component of the polymerization catalyst system.

In some aspects of this disclosure, adjusting the amount of one of the components of the polymerization catalyst system can modify the residence time in a vessel (e.g., a reactor, or a precontactor) of at least one of the components of the polymerization catalyst system, and as such the one or more ratios of components of the polymerization catalyst system can still be different when compared to the one or more target ratios, even upon adjusting the amount of one of the components of the polymerization catalyst system. In such aspects, the processor can continue to signal the at least one controller and direct the at least one controller to correct the one or more ratios of components of the polymerization catalyst system by adjusting an amount of at least one component of the polymerization catalyst system until the target ratios are met.

In an embodiment, the polymerization catalyst system comprises a solid component comprising an activator support. In such embodiment, the concentration of the activator support in the reactor feed stream can be used for calculating one or more ratios of components of the polymerization catalyst system, wherein the concentration of the activator support was calculated by using turbidimeter measurements as disclosed herein. The one or more ratios of components of the polymerization catalyst system can be compared to one or more target ratios.

In an embodiment, the catalyst comprises at least one metallocene. In such embodiment, translating the turbidity of the reactor feed stream into a concentration of the activator support in the reactor feed stream further comprises subtracting a background signal of the at least one metallocene from the measured turbidity of the reactor feed stream.

In an embodiment, the concentration of the activator support in the reactor feed stream can be used for calculating a ratio of activator support/catalyst, a ratio of activator support/co-catalyst, or both. The ratio of activator support/catalyst can be compared to a target ratio of activator support/catalyst. The ratio of activator support/co-catalyst can be compared to a target ratio of activator support/co-catalyst.

In some embodiments, the ratio of activator support/catalyst can be different when compared to a target ratio of activator support/catalyst, and the ratio of activator support/co-catalyst can be the same when compared to the target ratio of activator support/co-catalyst. In such embodiment, the amount of catalyst can be adjusted to meet the target ratio of activator support/catalyst. When the catalyst comprises at least one metallocene, adjusting the amount of metallocene can trigger a change in the residence time of the activator support in a vessel (e.g., a reactor, or a precontactor), and as such the other ratios (e.g., activator support/organoaluminum co-catalyst ratio) could be inadvertently modified, thereby requiring further correction of the one or more ratios of components of the polymerization catalyst system until all target ratios are met.

In other embodiments, the ratio of activator support/catalyst can be the same when compared to the target ratio of activator support/catalyst, and the ratio of activator support/co-catalyst can be different when compared to the target ratio of activator support/co-catalyst. In such embodiments, the amount of co-catalyst can be adjusted to meet the target ratio of activator support/co-catalyst. When the co-catalyst comprises an organoaluminum compound, adjusting the amount of organoaluminum compound can trigger a change in the residence time of the activator support in a vessel (e.g., a reactor, or a precontactor), and as such the other ratios (e.g., activator support/catalyst ratio) could be inadvertently modified, thereby requiring further correction of the one or more ratios of components of the polymerization catalyst system until all target ratios are met.

In yet other embodiments, the ratio of activator support/catalyst can be different when compared to the target ratio of activator support/catalyst, and the ratio of activator support/co-catalyst can different when compared to the target ratio of activator support/co-catalyst. In such embodiments, the amount of activator support can be adjusted to meet the target ratio of activator support/catalyst and the target ratio of activator support/co-catalyst. When the polymerization catalyst system comprises at least one metallocene, adjusting the amount of activator support can trigger a change in the residence time of the activator support in a vessel (e.g., a reactor, or a precontactor), thereby requiring further correction of the one or more ratios of components of the polymerization catalyst system until all target ratios are met.

In some aspects, the polymerization catalyst system can comprise more than one catalyst, such as for example in the case of a dual metallocene catalyst system, wherein the catalyst comprises a first metallocene and a second metallocene. As will be appreciated by one of skill in the art, and with the help of this disclosure, when more than one catalyst is used for the polymerization, the concentration of each catalyst can be used for calculating activator support/catalysts ratios, and the ratios of the components of the polymerization catalyst system can be compared to the corresponding target ratios of the components of the polymerization catalyst system, followed by adjusting as necessary concentrations/amounts of components of the polymerization catalyst system to meet the target ratios, in a manner similar to the case when the polymerization catalyst system comprises one catalyst.

For example, the concentration of the activator support in the reactor feed stream can be used for calculating a ratio of activator support/first metallocene, a ratio of activator support/second metallocene, a ratio of activator support/co-catalyst, or combinations thereof. The ratio of activator support/first metallocene can be compared to a target ratio of activator support/first metallocene. The ratio of activator support/second metallocene can be compared to a target ratio of activator support/second metallocene. The ratio of activator support/co-catalyst can be compared to a target ratio of activator support/co-catalyst. As will be appreciated by one of skill in the art, and with the help of this disclosure, when the catalyst comprises at least two metallocenes, there is a desired preset ratio between the metallocene components of the catalyst (based on the desired polymer end-product), and as such an amount of the individual metallocene components can be independently adjusted as necessary provided that the preset ratio between the metallocene components does not change.

The various embodiments shown in the Figures can be simplified and may not illustrate common equipment such as heat exchangers, pumps, and compressors; however, a skilled artisan would recognize the disclosed processes and systems can include such equipment commonly used throughout polymer manufacturing.

A skilled artisan will recognize that industrial and commercial polyethylene manufacturing processes can necessitate one or more, often several, compressors or similar apparatuses. Such compressors are used throughout polyethylene manufacturing, for example (and with reference to FIG. 1) to pressurize reactors 104, 106 during polymerization. Further, a skilled artisan will recognize that a polyethylene manufacturing process includes one or more deoxygenators, similar de-oxidizing apparatuses, or both, for instance for purifying solvents or reactants, for purging reactors of oxygen, or both. Because the infrastructure and the support therefore, for example to provide power and maintain the compressors, the deoxygenators, or both, already exists within a commercial polyethylene manufacturing plant, reallocating a portion of these available resources for use in the disclosed systems can necessitate little, if any, additional capital expenditure in order to incorporate the disclosed systems and or processes.

Further, because compressors, deoxygenators, and various other components are already employed in various polyethylene production processes and systems, the opportunity for increased operation of such apparatuses can improve the overall efficiency of polyethylene production systems and processes. For example, when a portion of a polyethylene production process or system is taken off-line for maintenance, repair, or both, other portions of the system (e.g., a compressor, a deoxygenator, or a reactor) can continue to provide service according to the current processes. Operating, reallocating resources, or both for operation of the disclosed polyethylene production systems, polyethylene production processes, or both can thereby increase the efficiency with which conventional systems are used.

Figure 2:
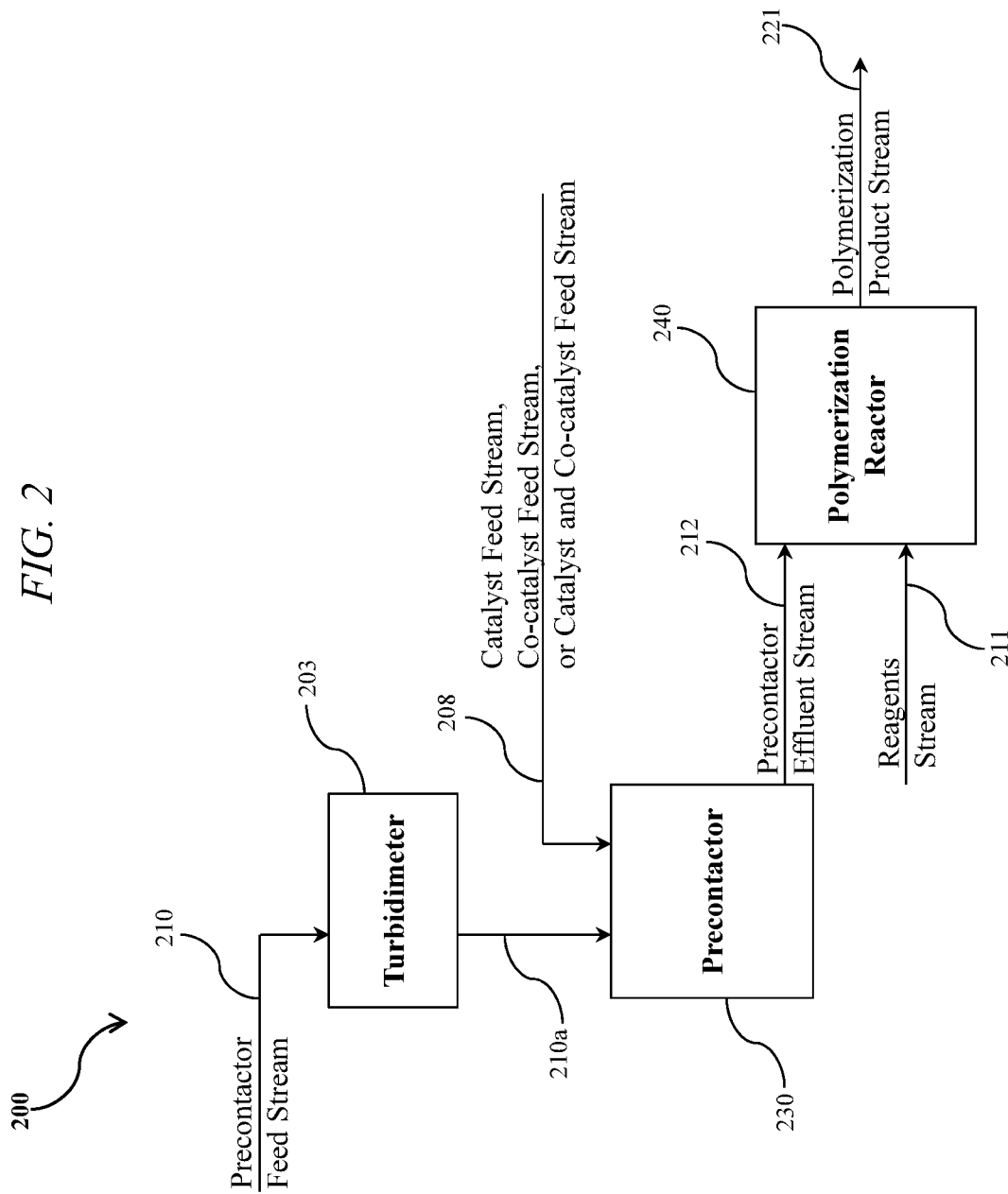
FIG. 2 illustrates a schematic of an embodiment of a polyethylene production system comprising a turbidimeter upstream of a precontactor.

In an aspect of this disclosure, a method of monitoring a solid component of a reactor feed stream can be carried out in a polyethylene production system, such as for example a polyethylene production system 200 illustrated in the embodiment of FIG. 2. The polyethylene production system 200 generally comprises a turbidimeter 203, a precontactor 230, and a polymerization reactor 240. In the polyethylene production system embodiments disclosed herein, various system components can be in fluid communication via one or more conduits (e.g., pipes, tubing, or flow lines) suitable for the conveyance of a particular stream, for example as shown in detail by the numbered streams in FIGS. 2 and 3.

Referring to the embodiment of FIG. 2, at least a portion of a precontactor feed stream 210 (e.g., activator support stream) can be communicated to the turbidimeter 203 to measure the turbidity of the stream, as previously described herein. Upon measuring the turbidity of the feed stream, the turbidimeter 203 can communicate the precontactor feed stream (e.g., via precontactor feed stream 210a) to the precontactor 230.

As will be appreciated by one of skill in the art, and with the help of this disclosure, the precontactor feed stream 210 and the precontactor feed stream 210a have the same turbidity. The precontactor feed stream 210 and the precontactor feed stream 210a are essentially the same stream, wherein precontactor feed stream 210 is the precontactor feed stream prior to the turbidity measurement, and wherein precontactor feed stream 210a is the precontactor feed stream subsequent to the turbidity measurement.

In some embodiments, a portion of the precontactor feed stream can be routed from the feed stream through a turbidimeter (e.g., through a measuring flow cell of a turbidimeter) to measure the turbidity of the feed stream. Upon measuring the turbidity, the portion of the precontactor feed stream that was routed from the feed stream through the turbidimeter can be returned to the precontactor feed stream and can be communicated to the precontactor as part of the feed stream. Alternatively, the portion of the precontactor feed stream that was routed from the feed stream through the turbidimeter can be communicated to the precontactor without mixing with the precontactor feed stream that it was removed from prior to the turbidity measurement.

With continued reference to the embodiment of FIG. 2, a catalyst feed stream, a co-catalyst feed stream, or a catalyst and co-catalyst feed stream 208 can be communicated to the precontactor 230. A precontactor effluent stream 212 (e.g., a polymerization catalyst system feed stream, a reactor feed stream, or reactor feed stream 12a as in the embodiment of FIG. 1) can be communicated from the precontactor 230 to the polymerization reactor 240 (e.g., loop slurry reactor 104, or loop slurry reactors 104, 106 in the embodiment of FIG. 1). A reagents stream 211 (e.g., purified feed stream 11 in the embodiment of FIG. 1) can also be communicated to the polymerization reactor 240. A polymerization product stream 221 (e.g., polymerization product stream 121 in the embodiment of FIG. 1) can be emitted from the polymerization reactor 240.

In an embodiment, a method of monitoring a solid component (e.g., an activator support) of a reactor feed stream in a polyethylene production system 200 can comprise the steps of (a) measuring a turbidity of a precontactor feed stream 210, wherein the precontactor feed stream comprises an activator support of a metallocene-based catalyst system; and (b) translating the turbidity of the precontactor feed stream into a concentration of the activator support in a precontactor effluent stream 212 by using a calibration curve with known activator support concentration values as a function of measured turbidity, wherein the precontactor effluent stream comprises the reactor feed stream (e.g., polymerization catalyst system feed stream, metallocene-based catalyst system feed stream). In such embodiment, the metallocene-based catalyst system can comprise at least one metallocene catalyst and an organoaluminum compound co-catalyst. In an embodiment, the method of monitoring an activator support of a reactor feed stream in a polyethylene production system can further comprise calculating a mass balance across the precontactor to yield an amount of activator support in the precontactor; calculating a ratio of activator support/at least one metallocene, a ratio of activator support/organoaluminum compound, or both; and comparing the ratio of activator support/at least one metallocene to a target ratio of activator support/at least one metallocene, the ratio of activator support/organoaluminum compound to a target ratio of activator support/organoaluminum compound, or both.

Figure 3:
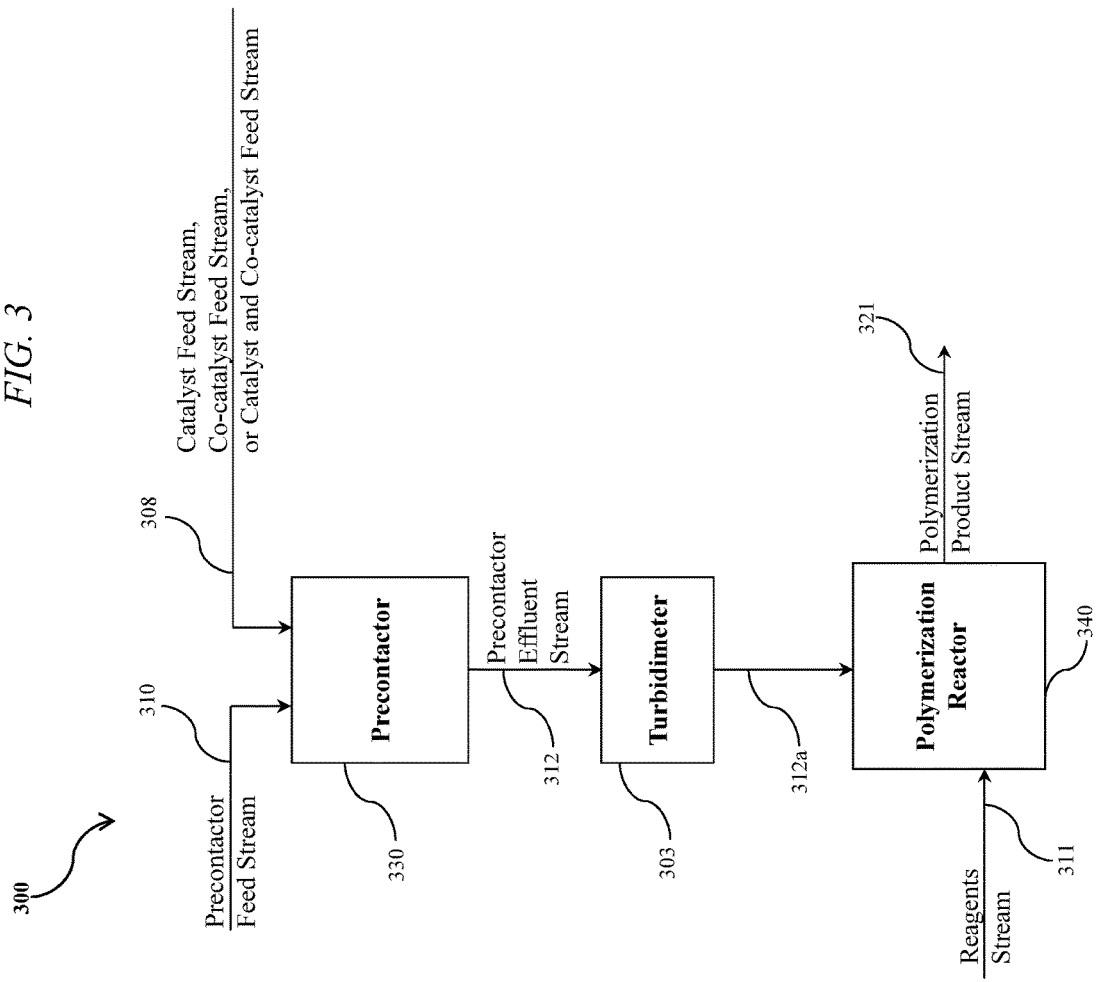
FIG. 3 illustrates a schematic of an embodiment of a polyethylene production system comprising a turbidimeter downstream of a precontactor.

In another aspect of this disclosure, a method of monitoring a solid component of a reactor feed stream can be carried out in a polyethylene production system, such as for example a polyethylene production system 300 illustrated in the embodiment of FIG. 3. The polyethylene production system 300 generally comprises a precontactor 330, a turbidimeter 303, and a polymerization reactor 340.

As illustrated generally in the embodiment of FIG. 3, a precontactor feed stream 310 (e.g., activator support stream); and a catalyst feed stream, a co-catalyst feed stream, or a catalyst and co-catalyst feed stream 308 can be communicated to the precontactor 330. At least a portion of a precontactor effluent stream 312 (e.g., a polymerization catalyst system feed stream, a reactor feed stream, the reactor feed stream 12 in the embodiment of FIG. 1) can be communicated from the precontactor 330 to the turbidimeter 303 to measure the turbidity of the stream, as previously described herein. Upon measuring the turbidity of the stream, the turbidimeter 303 can communicate the precontactor effluent stream 312*a* (e.g., a polymerization catalyst system feed stream, a reactor feed stream, reactor feed stream 12*a* in the embodiment of FIG. 1) to the to the polymerization reactor 340 (e.g., loop slurry reactor, reactors 104, 106 in the embodiment of FIG. 1).

As will be appreciated by one of skill in the art, and with the help of this disclosure, the precontactor effluent stream 312 and the precontactor effluent stream 312*a* have the same turbidity. The precontactor effluent stream 312 and the precontactor effluent stream 312*a* are essentially the same stream, wherein precontactor effluent stream 312 is the precontactor effluent stream prior to the turbidity measurement, and wherein precontactor effluent stream 312*a* is the precontactor feed stream subsequent to the turbidity measurement.

In some embodiments, a portion of the precontactor effluent stream can be routed from the stream through a turbidimeter (e.g., through a measuring flow cell of a turbidimeter) to measure the turbidity of the stream. Upon measuring the turbidity, the portion of the precontactor effluent stream that was routed from the stream through the turbidimeter can be returned to the precontactor effluent stream and can be communicated to the reactor as part of the precontactor effluent stream. Alternatively, the portion of the precontactor effluent stream that was routed from the effluent stream through the turbidimeter can be communicated to the reactor without mixing with the effluent stream that it was removed from prior to the turbidity measurement.

Referring to the embodiment of FIG. 3, a reagents stream 311 can be communicated to the polymerization reactor 340, and a polymerization product stream 321 can be emitted from the polymerization reactor 340.

In an embodiment, a method of monitoring a solid component (e.g., an activator support) of a reactor feed stream in a polyethylene production system 300 can comprise the steps of (a) measuring a turbidity of a precontactor effluent stream 312, wherein the precontactor effluent stream comprises an activator support of a metallocene-based catalyst system, at least one metallocene catalyst and an organoaluminum compound co-catalyst, and wherein the precontactor effluent stream comprises the reactor feed stream (e.g., polymerization catalyst system feed stream, such as a metallocene-based catalyst system feed stream); and (b) translating the turbidity of the precontactor effluent stream 312 into a concentration of the activator support in the reactor feed stream by using a calibration curve with known activator support concentration values as a function of measured turbidity. The concentration of the at least one metallocene catalyst and organoaluminum compound co-catalyst can be measured upstream of the precontactor. In such embodiment, measuring a turbidity of a precontactor effluent stream can further comprise subtracting a background signal of the at least one metallocene from the measured turbidity of the precontactor effluent stream.

In an embodiment, a polyethylene production system can comprise a polymerization catalyst system comprising at least one catalyst and an activator support, wherein the at least one catalyst, the activator support, or both can be a solid component of the polymerization catalyst system; a precontactor configured to receive the polymerization catalyst system via one or more precontactor feed streams, wherein at least one of the precontactor feed streams comprises at least a portion of the solid component; a precontactor effluent stream exiting the precontactor, wherein the precontactor effluent stream comprises at least a portion of the polymerization catalyst system; a polyethylene polymerization reactor configured to receive at least a portion of the precontactor effluent stream as a reactor feed stream, wherein the reactor feed stream comprises at least a portion of the solid component; and at least one turbidimeter for measuring a turbidity of a precontactor feed stream having a solid component therein, a turbidity of a precontactor effluent stream having a solid component therein, or both, wherein the turbidity of the precontactor feed stream, the turbidity of the precontactor effluent stream, or both are translated into a concentration of the solid component in the reactor feed stream.

In an embodiment, a method of monitoring a solid component of a reactor feed stream in a polyethylene production system can generally comprise the steps of (a) measuring a turbidity of the reactor feed stream, wherein the reactor feed stream comprises a solid component comprising a chromium-silica catalyst; and (b) translating the turbidity of the reactor feed stream into a concentration of the chromium-silica catalyst in the reactor feed stream. In such embodiment, the polyethylene production system does not comprise a precontactor, as the chromium-silica catalyst can be fed directly to the reactor via the reactor feed stream comprising the catalyst.

In an embodiment, a method of monitoring a solid component of a reactor feed stream in a polyethylene production system can generally comprise the steps of (a) measuring a turbidity of the reactor feed stream by using a turbidimeter, wherein the reactor feed stream comprises a solid component comprising a chromium-silica catalyst, wherein the reactor feed stream comprises a gaseous carrier, and wherein the chromium-silica catalyst in a gas carrier can be fed to a gas phase reactor through a fixed volume metering device; and (b) translating the turbidity of the reactor feed stream into a concentration of the chromium-silica catalyst in the reactor feed stream. In such embodiment, the turbidimeter can be located upstream of the fixed volume metering device, downstream of the fixed volume metering device, or both.

In an embodiment, a method of monitoring a solid component of a reactor feed stream in a polyethylene production system can generally comprise the steps of (a) measuring a turbidity of the reactor feed stream, wherein the reactor feed stream comprises a solid component comprising a Ziegler-Natta catalyst; and (b) translating the turbidity of the reactor feed stream into a concentration of the Ziegler-Natta catalyst in the reactor feed stream. In such embodiment, the polyethylene production system does not comprise a precontactor, and the Ziegler-Natta catalyst can be fed directly to the reactor via the reactor feed stream comprising the catalyst. In such embodiment, a reactor feed stream comprising an organoaluminum co-catalyst can also be fed to the reactor, wherein the reactor feed stream comprising the co-catalyst can be the same as or different than the reactor feed stream comprising the catalyst.

In some embodiments, a method of monitoring a solid component (e.g., a Ziegler-Natta catalyst) of a reactor feed stream in a polyethylene production system can comprise the steps of (a) measuring a turbidity of a precontactor feed stream, wherein the precontactor feed stream comprises a Ziegler-Natta catalyst; and (b) translating the turbidity of the precontactor feed stream into a concentration of the Ziegler-Natta catalyst in a precontactor effluent stream by using a calibration curve with known Ziegler-Natta catalyst concentration values as a function of measured turbidity, wherein the precontactor effluent stream comprises the reactor feed stream (e.g., polymerization catalyst system feed stream, such as a Ziegler-Natta catalyst system feed stream). In such embodiment, the Ziegler-Natta catalyst system can comprise at least one Ziegler-Natta catalyst and an organoaluminum compound co-catalyst. In an embodiment, the method of monitoring a Ziegler-Natta catalyst of a reactor feed stream in a polyethylene production system can further comprise calculating a mass balance across the precontactor to yield an amount of Ziegler-Natta catalyst in the precontactor; calculating a ratio of a Ziegler-Natta catalyst/organoaluminum compound; and comparing the ratio of Ziegler-Natta catalyst/organoaluminum compound to a target ratio of Ziegler-Natta catalyst/organoaluminum compound.

In an embodiment, a method of monitoring a solid component (e.g., a Ziegler-Natta catalyst) of a reactor feed stream in a polyethylene production system can comprise the steps of (a) measuring a turbidity of a precontactor effluent stream, wherein the precontactor effluent stream comprises a Ziegler-Natta catalyst of a Ziegler-Natta catalyst system, and an organoaluminum compound co-catalyst, and wherein the precontactor effluent stream comprises the reactor feed stream (e.g., polymerization catalyst system feed stream, Ziegler-Natta catalyst system feed stream); and (b) translating the turbidity of the precontactor effluent stream into a concentration of the Ziegler-Natta catalyst in the reactor feed stream by using a calibration curve with known Ziegler-Natta catalyst concentration values as a function of measured turbidity. The concentration of the organoaluminum compound co-catalyst can be measured upstream of the precontactor.

In an embodiment, one or more of the disclosed systems (e.g., polyethylene production system), the disclosed methods, or both can advantageously display improvements in one or more system characteristics, method characteristics, or both when compared to otherwise similar systems, methods, or both lacking a step of measuring the turbidity of a reactor feed stream. In an embodiment, a turbidimeter as disclosed herein can advantageously allow for a more accurate monitoring of the amount of solid components fed to a polymerization reactor. Given that the properties of the desired end-product polymer depend in part on the ratios of the components of a polymerization catalyst system, it is advantageous to monitor accurately the ratios of the components of a polymerization catalyst system in a reactor.

In an embodiment, a turbidimeter as disclosed herein can advantageously provide for a near real-time indication of a storage tank comprising a solid component of a polymerization catalyst system running empty, when the turbidimeter is located downstream of the storage tank. Knowing when a storage tank runs empty can be advantageous as the situation can be resolved (e.g., the storage tank can be refilled) prior to negatively impacting the polymer production.

In an embodiment, a turbidimeter as disclosed herein can advantageously provide for diagnosing high or low pressure in a storage tank, discharge of slurry feed pump, or both, which indicates an abnormal condition in manufacturing equipment that can negatively impact a polymer production process. Additional advantages of the systems and/or methods for the production of a polyethylene polymer as disclosed herein can be apparent to one of skill in the art viewing this disclosure.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

EXAMPLES

The disclosure having been generally described, the following examples are given as particular embodiments of the disclosure and to demonstrate the practice and advantages thereof. It is understood that the examples are given by way of illustration and are not intended to limit the specification of the claims to follow in any manner.

All turbidity measurements were conducted with a TC007-1 turbidimeter obtained from Kemtrak (Stockholm, Sweden). The TC007-1 turbidimeter consists of a high pressure flow cell with two sapphire windows spaced 2 mm apart connected via fiber optic cables to an AlGaAs LED lamp (operating at 850 nm) and a detector contained within a control/display box. The flow cell is designed to measure attenuation of the light passing through the flow cell. Calibration constants in the instrument were all set to zero except for the linear term, which was set to 1.00000; readings were output in units of absorbance units, or "AU."

Example 1

The turbidity of slurries of solid components of polymerization catalyst systems was investigated. More specifically, turbidity calibration curves were constructed for solid component slurries of various known concentrations.

The turbidimeter flow cell was mounted in a vertical orientation and connected via rubber tubing to a Microtrac 158139-SVR small volume recirculator (from Leeds & Northrup) with a flow rate of about 2 liters per minute. The configuration of the turbidimeter flow cell was such that the slurry flowed downward through the flow cell. The entire recirculation system (having a recirculation reservoir) was flushed thoroughly with heptane, water (if needed to remove solids), n-propanol (to remove water), and finally more heptane until a good zero turbidity reading could be obtained. Upon finalizing experiments, the recirculation system was filled with water and a spoonful of ascorbic acid was added and allowed to circulate in order to neutralize any residual Cr(VI), then flushed again with n-propanol and heptane.

Heptane, n-propanol, and deionized water were used as obtained. Initial measurements were performed on raw (not calcined) sulfated alumina (S-SSA). All subsequent data were collected using calcined solids. S-SSA was calcined to 600° C. and two different samples (sample #1 and sample #2) were used for calibration data experiments. Sample #1 was calcined in a rotary calciner and sample #2 was calcined in a fluidized bed calciner. For mullite, SIRALOX® 40 silica alumina base was obtained already calcined to 600° C. in a rotary calciner from Sasol North America, Inc. (Houston, Tex., USA). For silica, EP10X silica was obtained from a commercial supplier and was calcined in a muffle furnace to 400° C. $Cr/SiO_2$, $Cr/Ti/SiO_2$, $Cr/Mg/Ti/SiO_2$, and Cr/F/

SiO$_2$ chromium on silica catalysts were obtained from commercial suppliers. Cr/SiO$_2$, Cr/Ti/SiO$_2$, and Cr/F/SiO$_2$ were calcined in a fluidized bed in air at 650° C., and Cr/Mg/Ti/SiO$_2$ was calcined in a fluidized bed in air at 625° C.

After an initial test of the experimental setup to confirm that all equipment was functioning as expected and that reasonable readings could be obtained, the calibration data was collected in a series of runs. Each run was performed by thoroughly flushing the recirculation system as described above, draining completely, adding 100 mL of fresh heptane (carrier fluid) to the recirculation system, zeroing the turbidimeter (if necessary), weighing aliquots of the desired solid (e.g., solid component of a polymerization catalyst system) into the recirculation system, and reading the turbidity from the instrument between aliquots. The solids were typically weighed by first adding 10.0 grams to a metal pan, then transferring a spoonful into the recirculator and weighing the solid remaining in the pan. This resulted in a typical run having solids concentrations from 0-10 g/100 mL (equivalent to 0-10 w/v %). Less than 10.0 grams of the desired solid was available for certain runs. Aliquots of solid were added until the pan was empty.

It should be noted that heptane is volatile, and in some cases the volume of liquid in the recirculation system could be seen to be decreasing as the runs were carried out. Therefore runs were performed as quickly as possible. It should be further noted that in most cases some solid could be seen to stick to the sidewalls of the recirculation reservoir, particularly at the highest solids concentrations. An effort was made to keep this sedimentation to a minimum by scraping the solids back into the slurry as needed, but this negatively affected the speed with which data could be collected. However, the data were found to be acceptably reproducible, with the data at the lower solids concentrations being more reproducible.

Figure 4A:
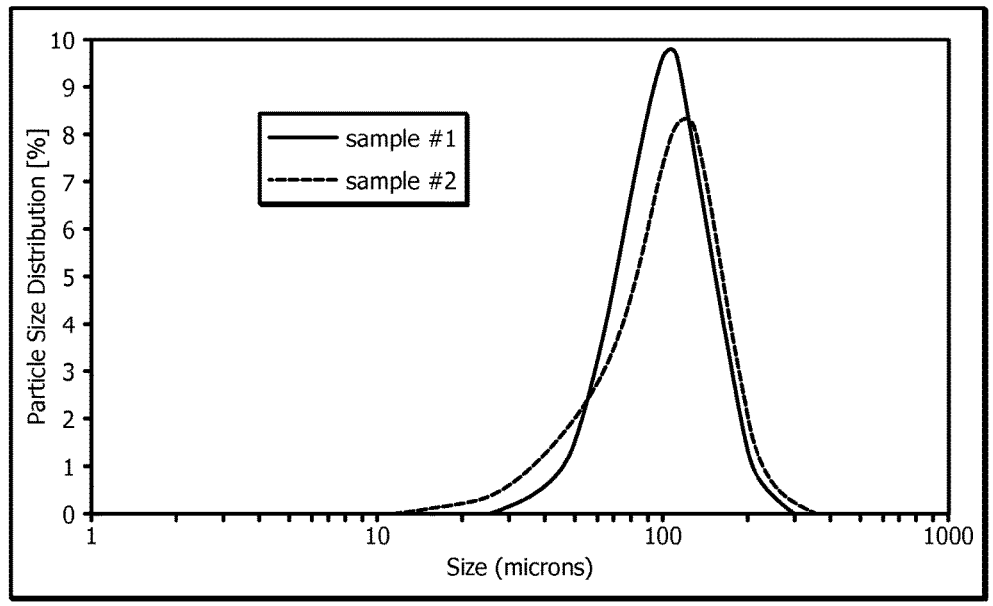
FIG. 4A displays a graph of particle size distribution for two sulfated alumina (S-SSA) samples.

As particle size distribution has the potential to affect turbidity measurements, the particle size distribution for two samples of S-SSA (sample #1 and sample #2) were recorded using a Microtrac FRA9200 particle size analyzer (available from Microtrac, Montgomery, Pa., USA) and the data are displayed in FIG. 4A.

Sample #1 and sample #2 were further subjected to turbidity measurements, and the data are displayed in Table 1 for sample #1 (four different runs) and in Table 2 for sample #2 (three different runs). The turbidity data are summarized for both sample #1 and sample #2 in FIG. 5.

TABLE 1

| S-SSA Sample #1 | | | |
|---|---|---|---|
| Run #1 | | Run #2 | |
| Turbidity [AU] | Concentration [g/100 mL] | Turbidity [AU] | Concentration [g/100 mL] |
| 0 | 0 | 0 | 0 |
| 0.203 | 0.73 | 0.286 | 1.12 |
| 0.426 | 1.49 | 0.632 | 2.15 |
| 0.70 | 2.28 | 0.82 | 2.70 |
| 0.94 | 3.49 | 1.10 | 3.51 |
| 1.19 | 4.50 | 1.33 | 4.21 |
| 1.55 | 5.52 | 1.50 | 5.10 |
| 1.99 | 6.70 | 1.70 | 5.91 |
| 2.36 | 7.77 | 2.06 | 7.22 |
| 2.60 | 8.70 | 2.41 | 8.42 |
| 2.83 | 10.0 | 2.73 | 10.0 |

TABLE 1-continued

| S-SSA Sample #1 | | | |
|---|---|---|---|
| Run #3 | | Run #4 | |
| Turbidity [AU] | Concentration [g/100 mL] | Turbidity [AU] | Concentration [g/100 mL] |
| 0 | 0 | 0 | 0 |
| 0.237 | 0.77 | 0.256 | 0.80 |
| 0.42 | 1.64 | 0.523 | 1.58 |
| 0.70 | 2.75 | 0.75 | 2.25 |
| 0.96 | 3.71 | 1.06 | 3.49 |
| 1.28 | 4.87 | 1.32 | 4.61 |
| 1.63 | 6.16 | 1.76 | 5.83 |
| 2.04 | 7.24 | 2.14 | 7.11 |
| 2.37 | 8.20 | 2.45 | 8.07 |
| 2.61 | 9.17 | 2.68 | 9.02 |
| 2.77 | 10.0 | 2.84 | 10.0 |

TABLE 2

| S-SSA Sample #2 | | | | | |
|---|---|---|---|---|---|
| Run #1 | | Run #2 | | Run #3 | |
| Turbidity [AU] | Concentration [g/100 mL] | Turbidity [AU] | Concentration [g/100 mL] | Turbidity [AU] | Concentration [g/100 mL] |
| 0 | 0 | 0 | 0 | 0 | 0 |
| 0.087 | 0.20 | 0.347 | 0.94 | 0.224 | 0.58 |
| 0.20 | 0.49 | 0.65 | 1.90 | 0.488 | 1.44 |
| 0.35 | 0.85 | 0.93 | 2.87 | 0.74 | 2.40 |
| 0.49 | 1.28 | 1.27 | 3.91 | 1.04 | 3.41 |
| 0.62 | 1.74 | 1.65 | 5.04 | 1.39 | 4.59 |
| 0.78 | 2.33 | 2.00 | 6.04 | 1.81 | 5.85 |
| 1.06 | 3.10 | 2.30 | 6.95 | 2.28 | 7.35 |
| 1.38 | 3.98 | 2.59 | 8.15 | 2.57 | 8.57 |
| 1.91 | 5.28 | 2.76 | 9.12 | 2.73 | 9.45 |
| 2.25 | 6.25 | 2.86 | 10.0 | 2.82 | 10.0 |
| 2.58 | 7.57 | — | — | — | — |
| 2.79 | 8.88 | — | — | — | — |
| 2.90 | 10.0 | — | — | — | — |

Figure 4B:
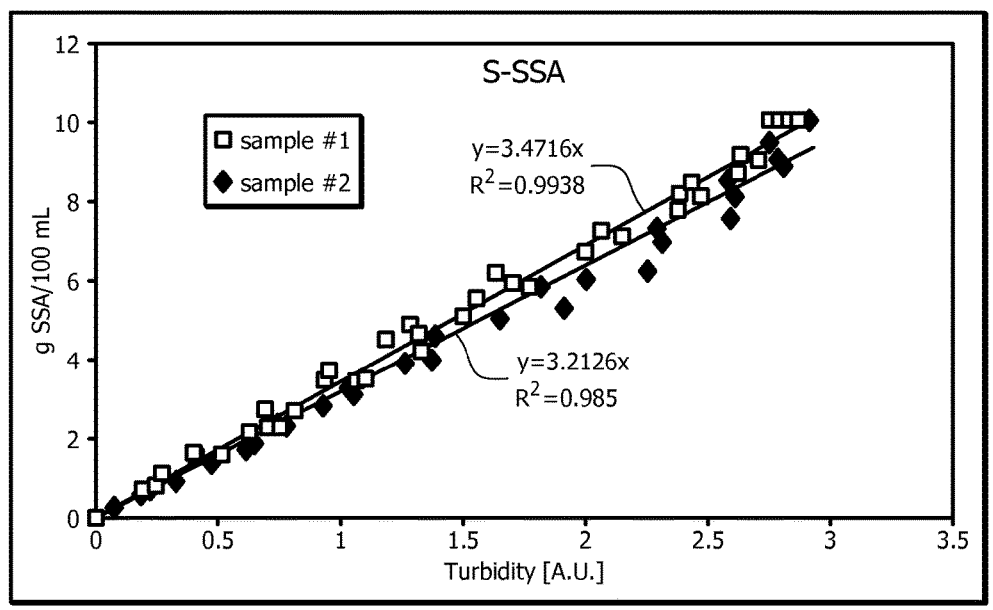
FIG. 4B displays a calibration curve graph with known S-SSA concentration values as a function of measured turbidity.

The relationship between S-SSA concentration in the slurry and turbidity was found to be very linear for the data collected using the S-SSA sample #1. As shown in FIG. 4A, the particle size distributions for both sample #1 and sample #2 are similar to each other. As shown in FIG. 4B, the data for sample #1 produced an excellent linear fit, which differed from sample #2 by less than 10%, probably due to the similar particle size distribution for both sample #1 and sample #2.

Figure 5:
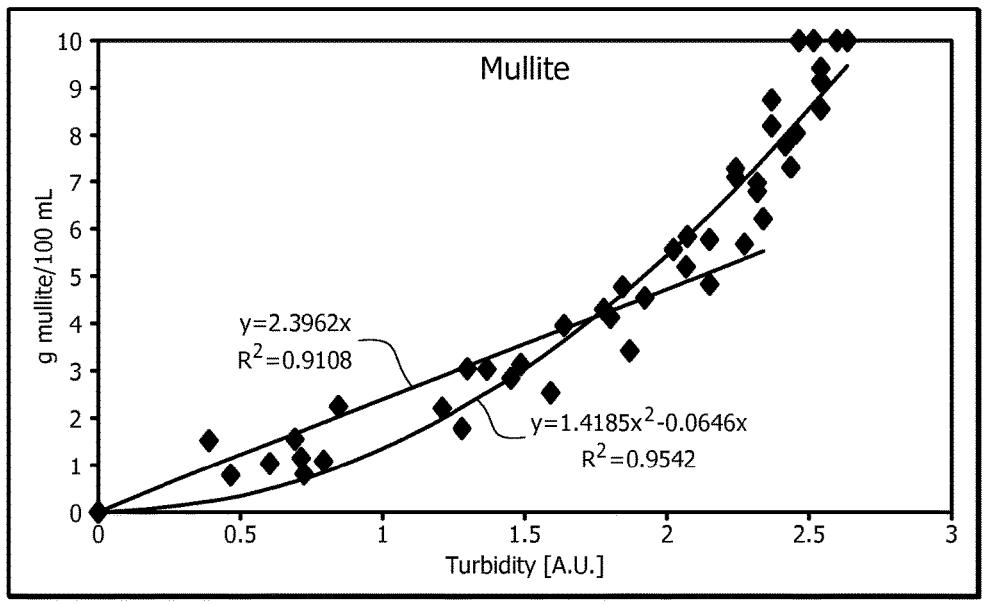
FIG. 5 displays a calibration curve graph with known mullite concentration values as a function of measured turbidity.

Mullite was also subjected to turbidity measurements, and the data are displayed in Table 3 (five different runs) and are summarized in FIG. 5.

TABLE 3

| Mullite | | | | | |
|---|---|---|---|---|---|
| Run #1 | | Run #2 | | Run #3 | |
| Turbidity [AU] | Conc. [g/100 mL] | Turbidity [AU] | Conc. [g/100 mL] | Turbidity [AU] | Conc. [g/100 mL] |
| 0 | 0 | 0 | 0 | 0 | 0 |
| 0.47 | 0.75 | 0.73 | 0.84 | 0.39 | 1.47 |
| 0.61 | 1.00 | 1.28 | 1.76 | 1.37 | 3.01 |

TABLE 3-continued

| Mullite | | | | | |
|---|---|---|---|---|---|
| 0.69 | 1.55 | 1.59 | 2.49 | 1.79 | 4.14 |
| 0.85 | 2.20 | 1.86 | 3.41 | 2.06 | 5.23 |
| 1.30 | 3.00 | 2.14 | 4.88 | 2.31 | 6.88 |
| 1.63 | 3.95 | 2.26 | 5.71 | 2.44 | 8.06 |
| 1.83 | 4.78 | 2.33 | 6.25 | 2.53 | 9.21 |
| 2.01 | 5.60 | 2.43 | 7.36 | 2.59 | 10.0 |
| 2.24 | 7.07 | 2.53 | 8.59 | — | — |
| 2.36 | 8.24 | 2.62 | 10.0 | — | — |
| 2.50 | 10.0 | — | — | — | — |

| Run #4 | | Run #5 | |
|---|---|---|---|
| Turbidity [AU] | Conc. [g/100 mL] | Turbidity [AU] | Conc. [g/100 mL] |
| 0 | 0 | 0 | 0 |
| 0.72 | 1.06 | 0.80 | 1.03 |
| 1.21 | 2.17 | 1.45 | 2.83 |
| 1.49 | 3.07 | 1.91 | 4.53 |
| 1.77 | 4.29 | 2.14 | 5.80 |
| 2.06 | 5.86 | 2.31 | 7.03 |
| 2.23 | 7.32 | 2.40 | 7.86 |
| 2.36 | 8.78 | 2.53 | 9.41 |
| 2.45 | 10.0 | 2.58 | 10.0 |

As shown in FIG. 5, the data follow a quadratic fit reasonably well, however, it must be noted that it was particularly difficult to prevent sedimentation of mullite at higher slurry concentrations. In some instances, only data at lower mullite concentrations could be used to produce mullite calibration curves, as there might be less uncertainty about the true concentration of the slurry. Further, as shown in FIG. 5, a linear fit could be obtained for mullite concentrations below 7 g/100 mL. Generally, a linear fit is easier to use than a quadratic fit, as the linear fit can allow for easier calculation of coefficients and standard deviations; easier correction factor calculation; easier tracking of analysis uncertainty; better correlation to a theoretical model for light absorption/scattering; or combinations thereof; when compared to a quadratic fit.

Figure 6:
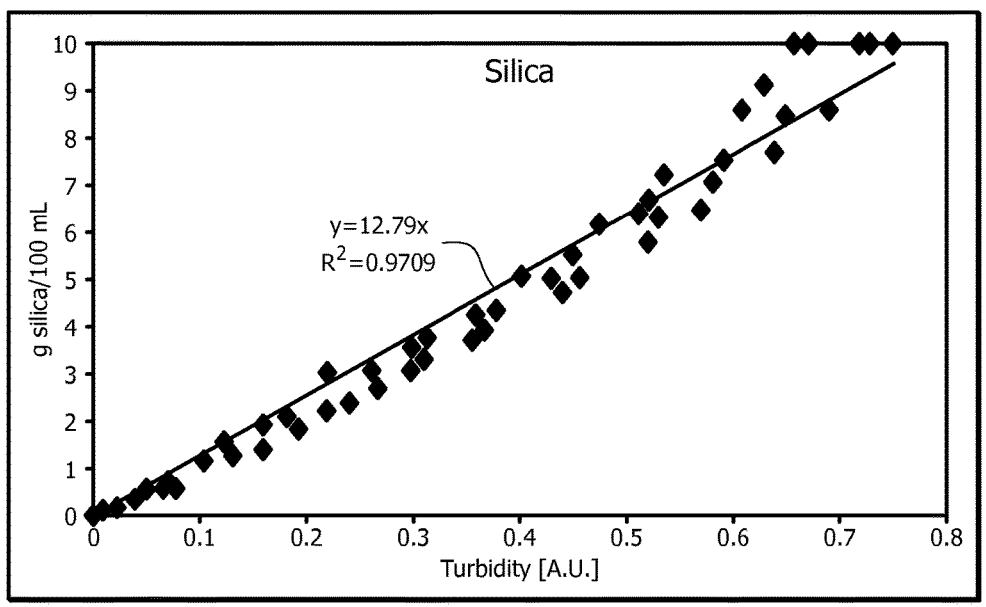
FIG. 6 displays a calibration curve graph with known silica concentration values as a function of measured turbidity.

As several chromium-based catalysts use a silica support, silica was also subjected to turbidity measurements, and the data are displayed in Table 4 (five different runs) and are summarized in FIG. 6.

TABLE 4

| Silica | | | | | |
|---|---|---|---|---|---|
| Run #1 | | Run #2 | | Run #3 | |
| Turbidity [AU] | Conc. [g/100 mL] | Turbidity [AU] | Conc. [g/100 mL] | Turbidity [AU] | Conc. [g/100 mL] |
| 0 | 0 | 0 | 0 | 0 | 0 |
| 0.011 | 0.10 | 0.079 | 0.59 | 0.051 | 0.57 |
| 0.023 | 0.20 | 0.162 | 1.41 | 0.105 | 1.17 |
| 0.041 | 0.38 | 0.241 | 2.39 | 0.184 | 2.10 |
| 0.070 | 0.71 | 0.10 | 3.34 | 0.262 | 3.09 |
| 0.125 | 1.51 | 0.38 | 4.36 | 0.313 | 3.77 |
| 0.16 | 1.95 | 0.45 | 5.56 | 0.403 | 5.07 |
| 0.22 | 3.02 | 0.52 | 6.71 | 0.475 | 6.18 |
| 0.30 | 3.58 | 0.58 | 8.13 | 0.535 | 7.23 |
| 0.36 | 4.26 | 0.63 | 9.14 | 0.608 | 8.61 |
| 0.43 | 5.06 | 0.66 | 10.0 | 0.67 | 10.0 |
| 0.51 | 6.41 | — | — | — | — |
| 0.59 | 7.56 | — | — | — | — |
| 0.72 | 10.0 | — | — | — | — |

| Run #4 | | Run #5 | |
|---|---|---|---|
| Turbidity [AU] | Conc. [g/100 mL] | Turbidity [AU] | Conc. [g/100 mL] |
| 0 | 0 | 0 | 0 |
| 0.066 | 0.60 | 0.041 | 0.36 |
| 01.94 | 1.90 | 0.132 | 1.26 |
| 0.268 | 2.72 | 0.221 | 2.23 |
| 0.358 | 3.71 | 0.299 | 3.09 |
| 0.44 | 4.75 | 0.369 | 3.90 |
| 0.52 | 5.80 | 0.456 | 5.04 |
| 0.57 | 6.50 | 0.53 | 6.34 |
| 0.64 | 7.71 | 0.58 | 7.08 |
| 0.69 | 8.62 | 0.65 | 8.46 |
| 0.75 | 10.0 | 0.73 | 10.0 |

As shown in FIG. 6, silica gave a fairly linear response. However, in order to check on whether chromium interferes with the turbidity measurements, several chromium-based catalysts utilizing a silica support were also subjected to turbidity measurements, and the data are displayed in Table 5 for $Cr/F/SiO_2$ (four different runs) and in Table 6 for $Cr/Mg/Ti/SiO_2$ (two different runs), $Cr/SiO_2$ (one run), and $Cr/Ti/SiO_2$ (one run). The data for the chromium-based catalysts are summarized in FIG. 7.

TABLE 5

| $Cr/F/SiO_2$ | | | | | | | |
|---|---|---|---|---|---|---|---|
| Run #1 | | Run #2 | | Run #3 | | Run #4 | |
| Turbidity [AU] | Conc. [g/100 mL] | Turbidity [AU] | Conc. [g/100 mL] | Turbidity [AU] | Conc. [g/100 mL] | Turbidity [AU] | Conc. [g/100 mL] |
| 0 | 0 | 0 | 0 | 0 | 0 | 0 | 0 |
| 0.097 | 0.58 | 0.106 | 0.88 | 0.074 | 0.73 | 0.214 | 0.93 |
| 0.219 | 1.35 | 0.172 | 1.82 | 0.215 | 1.77 | 0.373 | 2.00 |
| 0.371 | 2.40 | 0.228 | 2.47 | 0.311 | 2.85 | 0.417 | 2.74 |
| 0.548 | 3.78 | 0.340 | 3.52 | 0.396 | 4.10 | 0.466 | 3.86 |
| 0.692 | 5.14 | 0.435 | 4.56 | 0.507 | 5.34 | 0.583 | 4.95 |
| 0.794 | 6.20 | 0.501 | 5.49 | 0.595 | 6.48 | 0.655 | 5.95 |
| 0.898 | 7.42 | 0.557 | 5.98 | 0.718 | 7.44 | 0.763 | 6.93 |
| 1.00 | 8.91 | — | — | 0.835 | 8.50 | 0.861 | 7.86 |
| 1.07 | 10.0 | — | — | 0.926 | 10.0 | — | — |

TABLE 6

| Cr/Mg/Ti/SiO$_2$ | | | | Cr/Ti/SiO$_2$ | | Cr/SiO$_2$ | |
|---|---|---|---|---|---|---|---|
| Run #1 | | Run #2 | | Run #1 | | Run #1 | |
| Turbidity [AU] | Conc. [g/100 mL] | Turbidity [AU] | Conc. [g/100 mL] | Turbidity [AU] | Conc. [g/100 mL] | Turbidity [AU] | Conc. [g/100 mL] |
| 0 | 0 | 0 | 0 | 0 | 0 | 0 | 0 |
| 0.052 | 0.49 | 0.055 | 1.03 | 0.077 | 0.60 | 0.21 | 1.21 |
| 0.124 | 1.15 | 0.135 | 1.85 | 0.151 | 1.59 | 0.34 | 2.09 |
| 0.195 | 1.99 | 0.30 | 2.73 | 0.258 | 2.25 | 0.45 | 2.95 |
| 0.330 | 2.99 | 0.45 | 3.39 | 0.333 | 3.02 | 0.55 | 4.06 |
| 0.402 | 3.96 | 0.50 | 3.86 | 0.39 | 4.37 | 0.70 | 5.24 |
| 0.64 | 5.27 | 0.54 | 4.38 | 0.62 | 5.98 | 0.83 | 6.59 |
| 0.69 | 6.67 | 0.54 | 4.77 | 0.69 | 7.19 | 1.01 | 7.86 |
| 0.79 | 8.08 | 0.59 | 5.29 | — | — | 1.10 | 8.86 |
| — | — | 0.53 | 5.77 | — | — | 1.15 | 9.60 |

Figure 7:
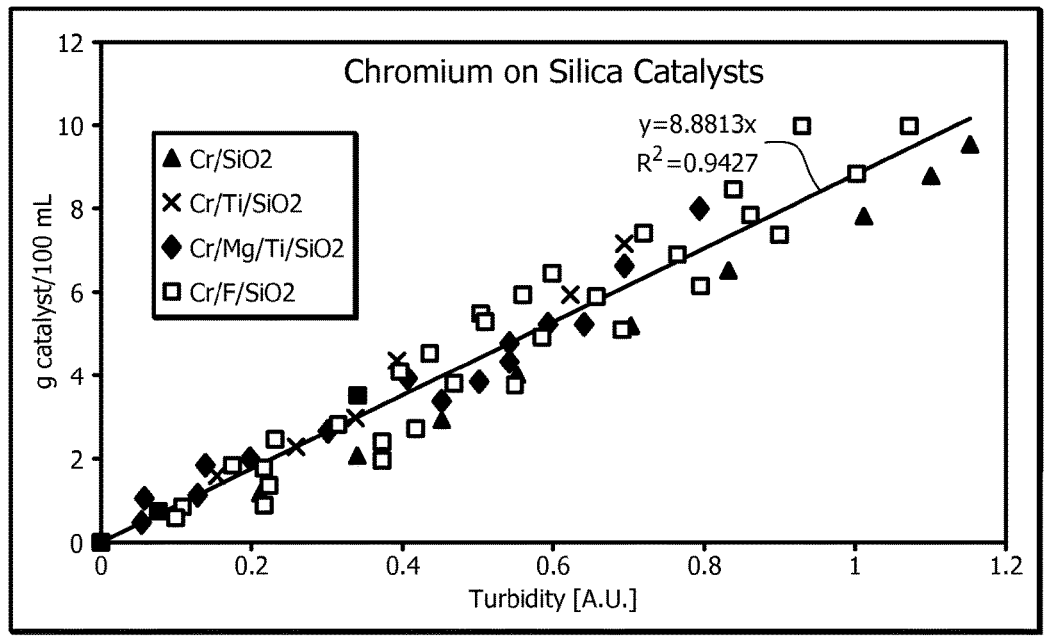
FIG. 7 displays a calibration curve graph with known chromium on silica concentration values as a function of measured turbidity.
Figure 8:
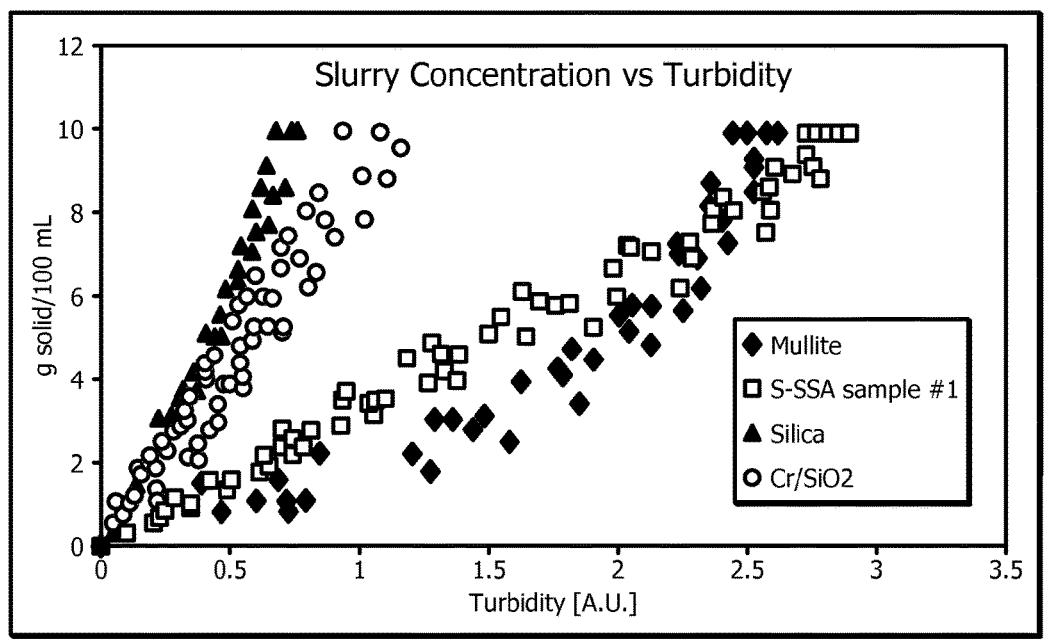
FIG. 8 displays a calibration curve graph with known solid components concentration values as a function of measured turbidity.

Tables 5 and 6, and FIG. 7 indicate that all data for all chromium-based catalysts can be fit quite well to a single linear regression, which can reduce or even eliminate the need for using individual calibration curves for different chromium-based catalysts. While the chromium-based catalysts displayed a different turbidity signal when compared to plain silica (as seen in FIG. 8), none of the modifications specific to a certain chromium-based catalyst resulted in a definitive change in turbidity. As such, a single calibration curve can be used for all chromium-based catalysts.

The data for all studied solid components of polymerization catalyst systems are summarized in FIG. 8. FIG. 8 shows the differences between each type of solid investigated, and indicates that each type of solid component requires a significantly different calibration curve. For example, the presence of chromium does affect the turbidity measurements of silica, as it can be seen by comparing the data point for silica and for Cr/SiO$_2$ in FIG. 8.

It should be noted that different solvents (carrier fluids) could have different refractive indices, and as such a correction factor could be necessary when using a calibration curve for a sample that is suspended in a carrier fluid different than the carrier fluid that was used for recording the calibration curve.

Example 2

Figure 9:
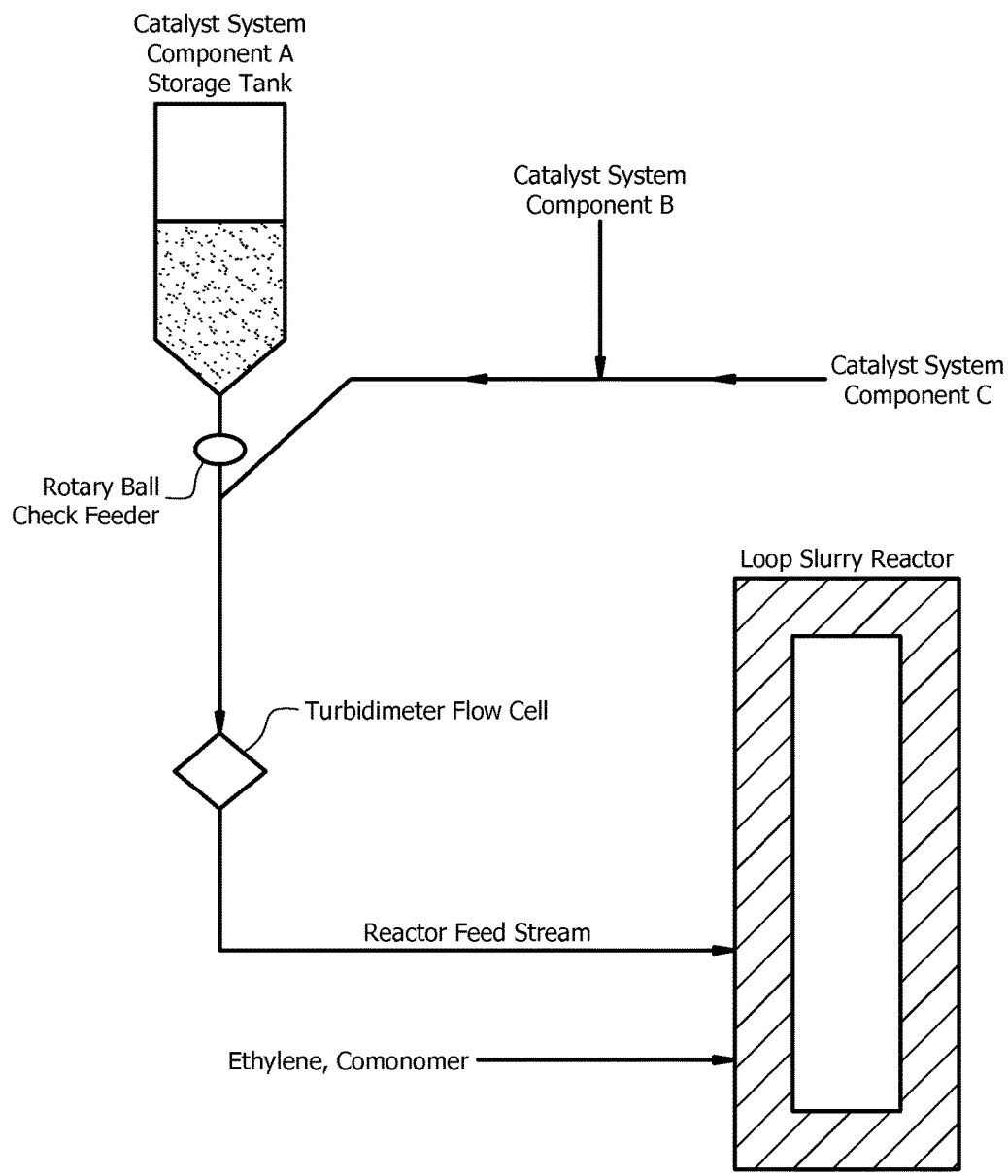
FIG. 9 illustrates a schematic of an embodiment of a polyethylene production system comprising a turbidimeter downstream of a storage tank.

The turbidity of activator support slurries was investigated. More specifically, a turbidimeter was integrated in a polyethylene production system as shown in FIG. 9, and was used for monitoring the turbidity of a reactor feed stream. An activator support (e.g., catalyst system component A, S-SSA or mullite) was slurried in isobutane in a storage tank (e.g., catalyst system component A storage tank). The activator support was dispensed from the storage tank via a rotary ball check feeder at specific time intervals. A catalyst (e.g., catalyst system component C, metallocene) and a co-catalyst (e.g., catalyst system component B, triisobutyl aluminum) were combined with each other prior to contacting the activator support stream dispensed by the rotary ball check feeder to produce a reactor feed stream. The reactor feed stream was analyzed by the turbidimeter flow cell prior to being communicated to the loop slurry reactor. Ethylene along with a comonomer (e.g., 1-hexene) was also communicated to the loop slurry reactor. The turbidimeter was zeroed with isobutane (carrier fluid) alone.

Figure 10A:
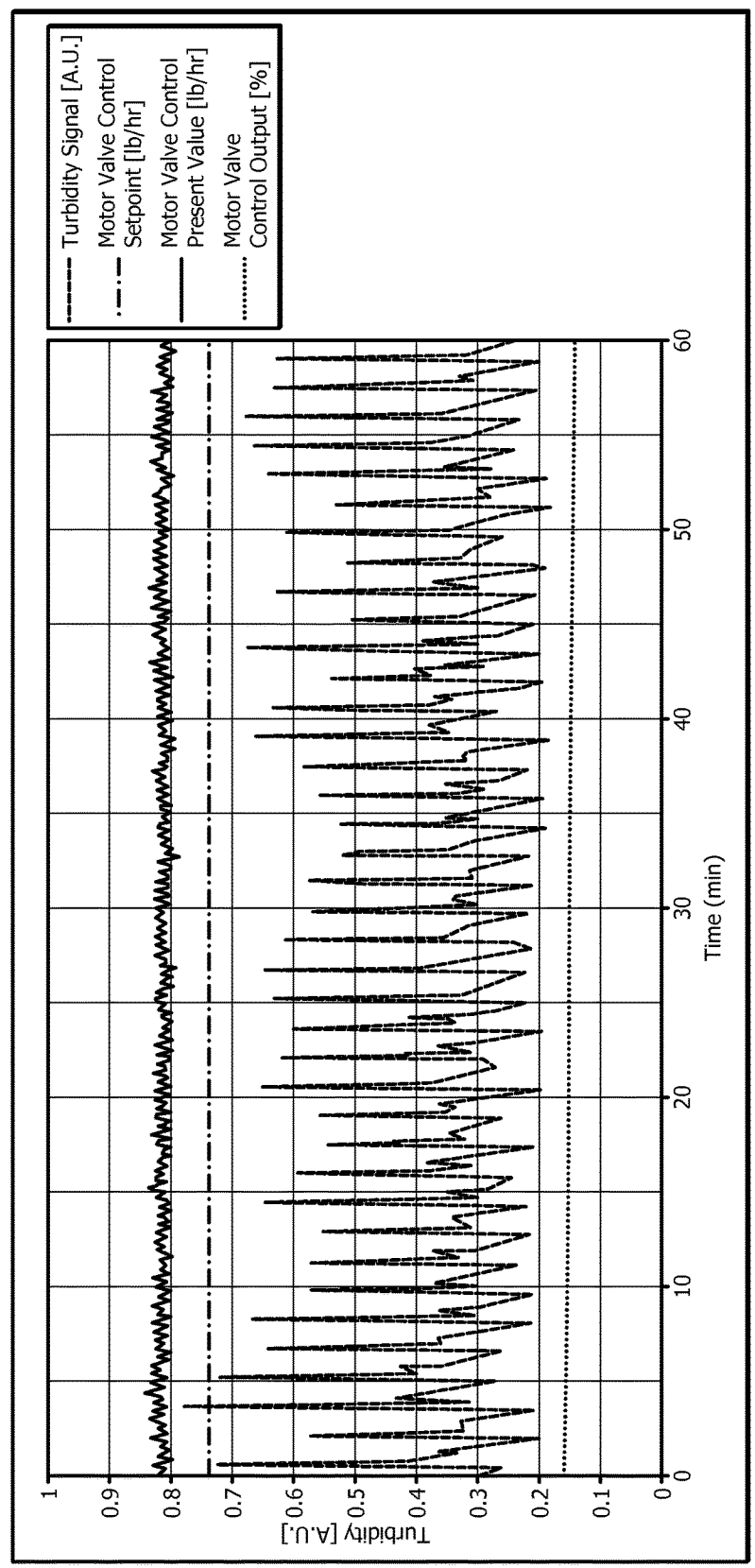
FIG. 10A displays a graph of a turbidimeter signal of an activator support dispensed from a storage tank at a frequency of 40 shots per hour.
Figure 10B:
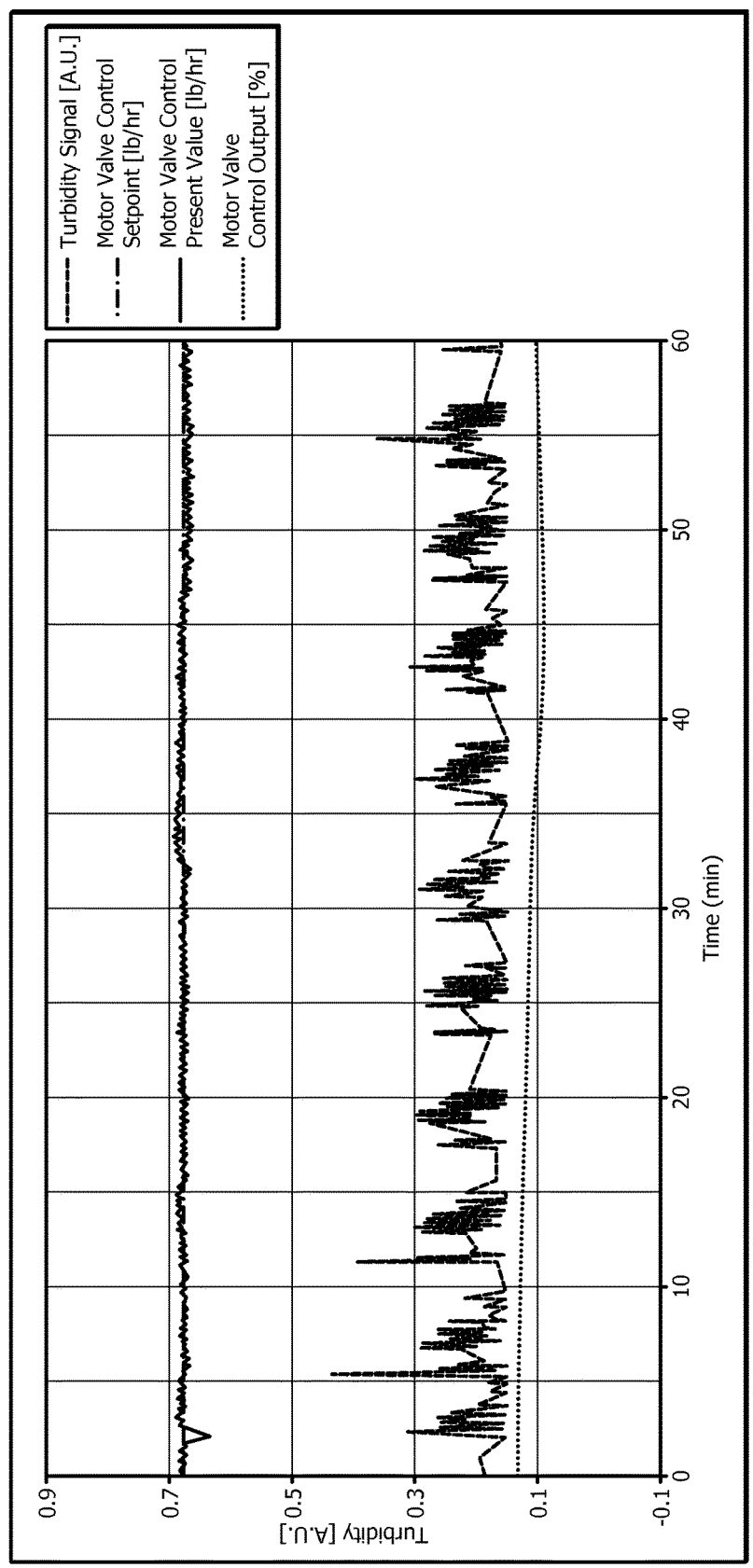
FIG. 10B displays a graph of a turbidimeter signal of an activator support dispensed from a storage tank at a frequency of 10 shots per hour.

The rotary ball check feeder was set to dispense the activator support with two different frequencies, 40 shots per hour and 10 shots per hour, and the raw data recorded by the turbidimeter are displayed in FIGS. 10A and 10B, respectively. The frequency of dispensing the activator support corresponds to the frequency of the rotary ball check feeder turning around and dispensing an aliquot of activator support slurries in the carrier fluid (e.g., isobutane). A lack of change in motor valve signals in FIGS. 10A and 10B indicates that the process has reached steady state operation and that turbidity signals over the same time window are indicative of the turbidity when the process reaches steady state.

FIGS. 10A and 10B display peaks corresponding to each activator support shot dispensed by the rotary ball check feeder. For the 40 shots per hour frequency of dispensing the activator support, the peaks display consistent heights and shapes, as shown in FIG. 10A. For the 10 shots per hour frequency of dispensing the activator support, the peaks display a dispersed appearance, as shown in FIG. 10B. Both frequencies of dispensing the activator support (e.g., catalyst flush rates) were performed under steady flow of carrier fluid (e.g., isobutane) of the solid support to the precontactor. These data highlight differences in the appearance (e.g., peak shape, peak height) of the raw turbidimeter signal output as a function of support type and other process parameters (e.g., carrier fluid flow rate). Despite these differences, the data can be used to adequately prescribe process conditions to maintain the desired ratios among support, catalyst, and co-catalyst.

Figure 11A:
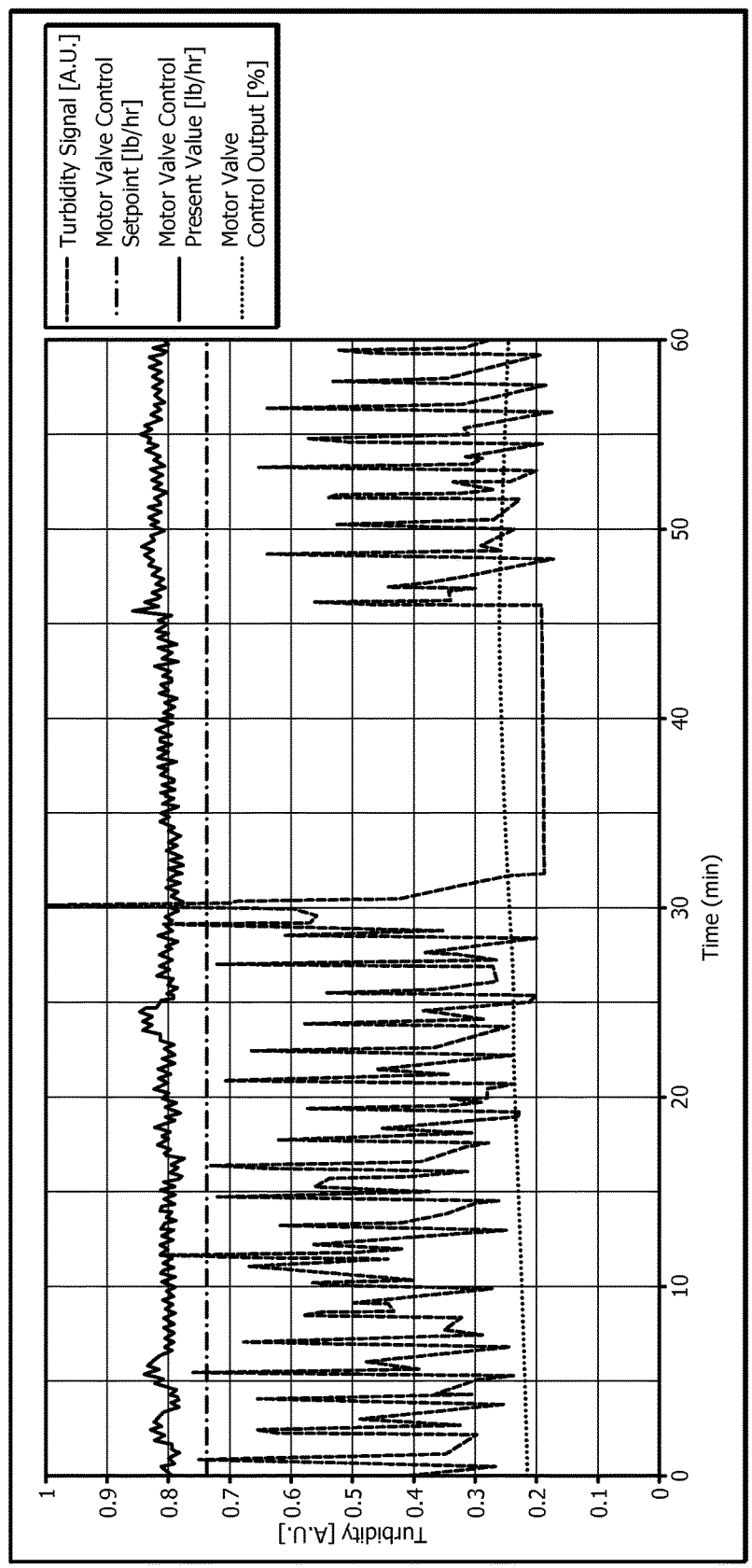
FIG. 11A displays a graph of a turbidimeter signal of an activator support dispensed from a storage tank indicating when the storage tank goes empty.
Figure 11B:
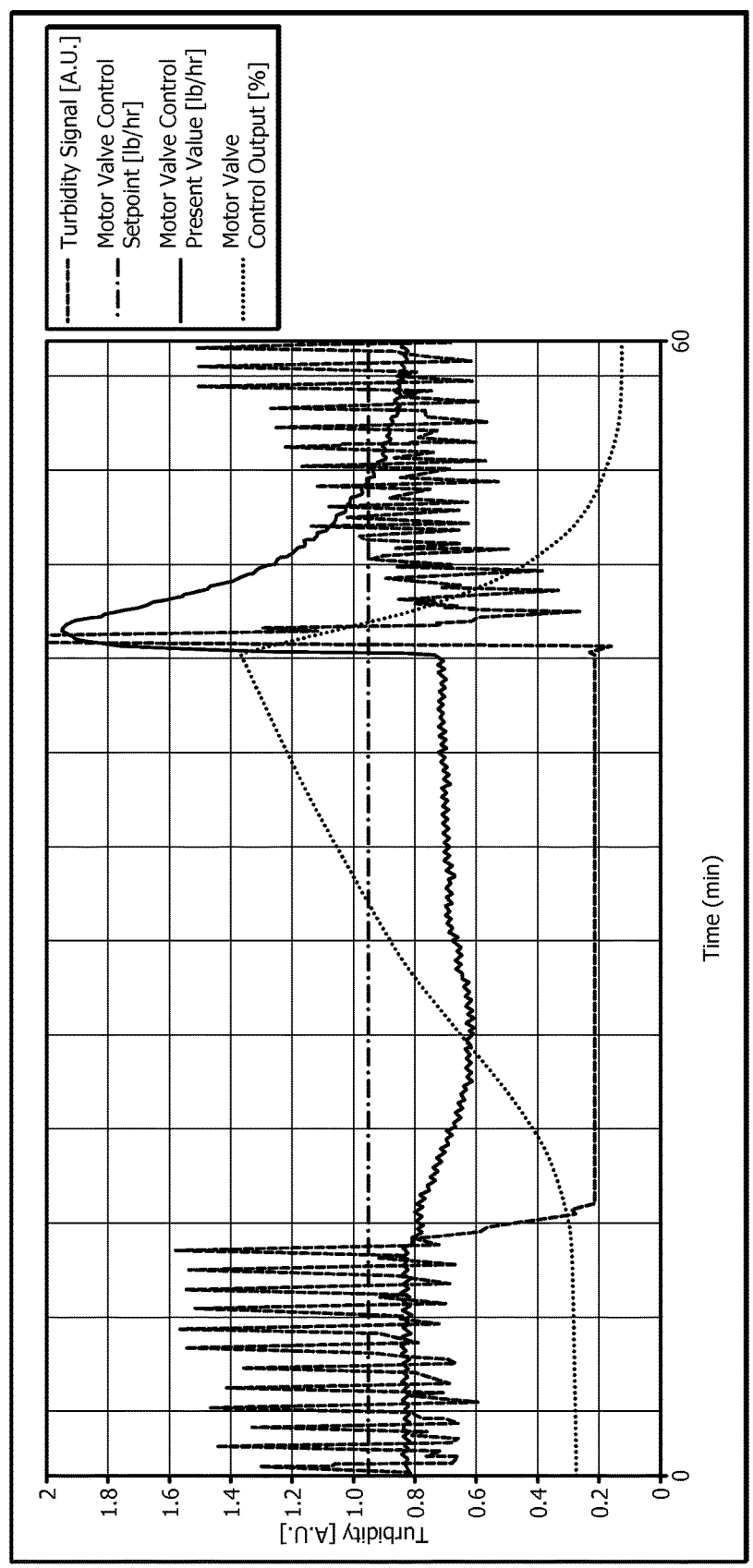
FIG. 11B displays a graph of a turbidimeter signal of an activator support dispensed from a storage tank indicating when the activator support flow has been interrupted.

FIGS. 11A and 11B display the raw data recorded by the turbidimeter when the activator support stopped flowing through the turbidimeter flow cell. FIG. 11A displays the raw data recorded by the turbidimeter when the activator support stopped flowing through the turbidimeter flow cell due to the storage tank running empty. As shown in FIG. 11A, the signal surged before going to zero to indicate a loss of activator support feed to the reactor. A surge in signal, as shown, can occur before a loss of feed but is not required to do so. Loss of turbidity signal to zero or a baseline level is a clear indication of the loss of support feed and is a consequence of such a loss in support feed. A lack of change in motor valve signals in FIG. 11A indicates that the rest of the system is functioning as it should and that the loss of turbidity signal observed in FIG. 11B is due to a loss of support feed which is, in turn, due to a catalyst storage vessel (e.g., storage tank) from which the feed is administered going empty, rather than some excursion in normal operation, such as a feed plug observed in FIG. 11B.

FIG. 11B displays the raw data recorded by the turbidimeter when the activator support stopped flowing through the turbidimeter flow cell due to a plug in the feed line which resulted in stopping the flow of activator support through the turbidimeter. The loss of turbidity signal to a baseline level indicates positively that no flow of solid support was occurring. However, the increase in the motor valve control output for the carrier fluid (e.g., isobutane) during the time of loss in turbidity signal indicated a restriction building in the feed line (e.g., a feed plug formed). Such a distinction enabled efficient maintenance to rectify the problem and resume polymer production.

Additional Disclosure

A first embodiment, which is a method of monitoring a solid component of a reactor feed stream in a polymer production system, comprising (a) measuring a turbidity of the reactor feed stream, wherein the reactor feed stream comprises a solid component of a polymerization catalyst system; and (b) translating the turbidity of the reactor feed stream into a concentration of the solid component in the reactor feed stream.

A second embodiment, which is the method of the first embodiment, wherein (b) translating the turbidity of the reactor feed stream into a concentration of the solid component in the reactor feed stream comprises using a calibration curve with known solid component concentration values as a function of measured turbidity.

A third embodiment, which is the method of any one of the first and the second embodiments, wherein (b) translating the turbidity of the reactor feed stream into a concentration of the solid component in the reactor feed stream further comprises subtracting a background signal from the measured turbidity of the reactor feed stream.

A fourth embodiment, which is the method of any of the first through the third embodiments, wherein (a) measuring a turbidity of the reactor feed stream comprises passing at least a portion of the feed stream through a turbidimeter, and obtaining an output signal representing turbidity from the turbidimeter.

A fifth embodiment, which is the method of the fourth embodiment, wherein the turbidimeter is located downstream of a solid component delivery device, wherein the solid component delivery device provides for intermittent delivery of the solid component into the reactor feed stream.

A sixth embodiment, which is the method of the fifth embodiment, wherein the solid component delivery device comprises a rotary ball check feeder.

A seventh embodiment, which is the method of any one of the first through the sixth embodiments, wherein the turbidimeter is located downstream of a solid component delivery device, wherein the solid component delivery device provides for continuous delivery of the solid component into the reactor feed stream.

An eighth embodiment, which is the method of any one of the first through the seventh embodiments, wherein the turbidity of the reactor feed stream, the concentration of the solid component in the reactor feed stream, or both are averaged over a time period to yield an averaged turbidity, an averaged concentration, or both.

A ninth embodiment, which is the method of the eighth embodiment, wherein the time period is from about 10 seconds to about 4 hours.

A tenth embodiment, which is the method of any one of the first through the ninth embodiments, wherein the time period is a residence time of the solid component in a reactor.

An eleventh embodiment, which is the method of any one of the first through the ninth embodiments, wherein the time period is a residence time of the solid component in a precontactor, wherein the precontactor is configured to receive at least a portion of two or more components of the polymerization catalyst system, and wherein one of the two or more components of the polymerization catalyst system comprises the solid component.

A twelfth embodiment, which is the method of the eleventh embodiment, wherein the turbidity is measured upstream of the precontactor, downstream of the precontactor, or both.

A thirteenth embodiment, which is the method of any one of the first through the twelfth embodiments, wherein a mass balance is calculated across the precontactor to yield an amount of solid component in the precontactor.

A fourteenth embodiment, which is the method of any one of the first through the thirteenth embodiments, wherein two or more components of the polymerization catalyst system can contact each other upstream of the precontactor.

A fifteenth embodiment, which is the method of any one of the first through the fourteenth embodiments, wherein the solid component is stored in a storage tank upstream of a reactor, and wherein the turbidity of the reactor feed stream is measured downstream of the storage tank.

A sixteenth embodiment, which is the method of the fifteenth embodiment, wherein a mass balance is calculated across the storage tank to yield an amount of the solid component in the storage tank.

A seventeenth embodiment, which is the method of any one of the first through the sixteenth embodiments, wherein a mass balance is calculated across the storage tank to yield a correlation factor, wherein the correlation factor is used with a calibration curve for (b) translating the turbidity of the reactor feed stream into a concentration of the solid component in the reactor feed stream.

An eighteenth embodiment, which is the method of any one of the first through the seventeenth embodiments, wherein the reactor feed stream enters a polymerization reactor, a loop slurry reactor, or a gas phase reactor.

A nineteenth embodiment, which is the method of any one of the first through the eighteenth embodiments, wherein the concentration of the solid component is used for calculating one or more ratios of components of the polymerization catalyst system.

A twentieth embodiment, which is the method of the nineteenth embodiment, wherein the one or more ratios of components of the polymerization catalyst system are compared to one or more target ratios.

A twenty-first embodiment, which is the method of the twentieth embodiment, wherein the one or more ratios of components of the polymerization catalyst system are different when compared to the one or more target ratios, and wherein an amount of at least one component of the polymerization catalyst system is adjusted to meet the target ratios.

A twenty-second embodiment, which is the method of any one of the first through the twenty-first embodiments, wherein the solid component comprises a chromium-based catalyst.

A twenty-third embodiment, which is the method of any one of the first through the twenty-second embodiments, wherein the chromium-based catalyst comprises chromium (VI).

A twenty-fourth embodiment, which is the method of any one of the first through the twenty-third embodiments, wherein the chromium-based catalyst comprises a support material and a chromium compound.

A twenty-fifth embodiment, which is the method of the twenty-fourth embodiment, wherein the support material comprises an inorganic oxide, silica, alumina, silica-alumina, titania, silica-titania, alumina-titania, aluminophosphate, aluminophosphate-titania, magnesia, zirconia, silica-zirconia, alumina-zirconia, ceria, ceria-zirconia, boria, thoria, clay, zeolites, mixed oxides thereof, or combinations thereof.

A twenty-sixth embodiment, which is the method of any one of the first through the twenty-fifth embodiments, wherein the chromium compound comprises chromium oxide, chromium trioxide, tertiary butyl chromate, a diarene chromium (0) compound, chromium acetates, chromium nitrates, chromium carboxylates, chromium naphthenates, chromium halides, chromium pyrrolides, chromium benzoates, chromium dionates, chromium sulfates, chromium (III) compounds, chromium (III) sulfate, chromium (III) chloride, chromium (III) nitrate, chromic bromide, chromium (III) acetylacetonate, chromium (III) acetate, chromium (III) isooctanoate, chromium (III) 2,2,6,6-tetramethylheptanedionate, chromium (III) naphthenate, chromium (III) tris(2-ethylhexanoate), chromic fluoride, chromium (III) oxy-2-ethylhexanoate, chromium (III) dichloroethylhexanoate, chromium (III) butyrate, chromium (III) neopentanoate, chromium (III) laurate, chromium (III) oxalate, chromium (III) benzoate, chromium (III) pyrrolide(s), chromium (III) perchlorate, chromium (III) chlorate, chromium (II) compounds, chromous fluoride, chromous chloride, chromous bromide, chromous iodide, chromium (II) sulfate, chromium (II) acetate, chromium (II) bis(2-ethylhexanoate), chromium (II) butyrate, chromium (II) neopentanoate, chromium (II) laurate, chromium (II) stearate, chromium (II) oxalate, chromium (II) benzoate, chromium (II) pyrrolide(s), chromous sulfate, biscyclopentadienyl chromium (II), or combinations thereof.

A twenty-seventh embodiment, which is the method of any one of the first through the twenty-sixth embodiments, wherein the chromium-based catalyst is characterized by a reactor residence time of from about 30 minutes to about 90 minutes.

A twenty-eighth embodiment, which is the method of the twenty-seventh embodiment, wherein the turbidity of the reactor feed stream, the concentration of the chromium-based catalyst in the reactor feed stream, or both are averaged over the reactor residence time to yield an averaged turbidity of the reactor feed stream, an averaged concentration of the chromium-based catalyst in the reactor feed stream, or both.

A twenty-ninth embodiment, which is the method of any one of the first through the twenty-first embodiments, wherein the solid component comprises an activator support.

A thirtieth embodiment, which is the method of the twenty-ninth embodiment, wherein the polymerization catalyst system comprises a catalyst comprising at least one metallocene.

A thirty-first embodiment, which is the method of any one of the twenty-ninth and the thirtieth embodiments, wherein the polymerization catalyst system further comprises a co-catalyst.

A thirty-second embodiment, which is the method of the thirty-first embodiment, wherein the co-catalyst comprises an organoaluminum compound, an alkylaluminum compound, a trialkylaluminum compound, triisobutylaluminum, tri-n-butylaluminum, tri-octyl-butylaluminum, triethylaluminum, trimethylaluminum, diethylaluminum ethoxide, diethylaluminum cyanide, alkyl-aluminum complexes, alkylaluminum halides, diethylaluminum chloride, diisobutylaluminum chloride, ethylaluminum sesquichloride, partially hydrolyzed alkylaluminum compounds, aluminoxanes, methylalumoxane, modified methylalumoxane, isobutyl alumoxanes, t-butyl alumoxanes, organoboron, triethylboron, organoborate compounds, organolithium compounds, ionizing ionic compounds, or combinations thereof.

A thirty-third embodiment, which is the method of any one of the twenty-ninth through the thirty-second embodiments, wherein the activator support comprises a clay mineral, dioctahedral (Al) clays, tri-octahedral (Mg) clays, bentonites, montmorillonites, mullites, allophanes, smectites, nontronites, hectorites, laponites, halloysites, vermiculites, micas, fluoromicas, chlorites, mixed-layer clays, fibrous clays, sepiolites, attapulgites, palygorskites, serpentine clays, illites, saponites, a pillared clay, an exfoliated clay, an exfoliated clay gelled into an oxide matrix, a layered silicate mineral, a non-layered silicate mineral, a layered aluminosilicate mineral, a non-layered aluminosilicate mineral, an ion-exchangeable clay, ion-exchangeable layered aluminosilicates, derivatives thereof, or combinations thereof.

A thirty-fourth embodiment, which is the method of any one of the twenty-ninth through the thirty-third embodiments, wherein the activator support comprises a solid oxide chemically-treated with an electron-withdrawing component.

A thirty-fifth embodiment, which is the method of the thirty-fourth embodiment, wherein the solid oxide comprises alumina ($Al_2O_3$), boria ($B_2O_3$), BeO, $Bi_2O_3$, $CeO_2$, CdO, $CO_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, silica ($SiO_2$), $SnO_2$, SrO, thoria ($ThO_2$), titania ($TiO_2$), $V_2O_5$, $WO_3$, $Y_2O_3$, zinc oxide (ZnO), zirconia ($ZrO_2$), magnesia (MgO), aluminum phosphate, aluminophosphate, heteropolytungstate, zeolites, silica-alumina, silica-coated alumina, silica-titania, coprecipitated silica/titania, silica-zirconia, alumina-titania, alumina-zirconia, zinc-aluminate, alumina-boria, silica-boria, aluminophosphate-silica, titania-zirconia, mixed oxides thereof, or combinations thereof.

A thirty-sixth embodiment, which is the method of any one of the twenty-ninth through the thirty-fifth embodiments, wherein the electron-withdrawing component comprises sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or combinations thereof.

A thirty-seventh embodiment, which is the method of any one of the twenty-ninth through the thirty-sixth embodiments, wherein the activator support comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, or combinations thereof.

A thirty-eighth embodiment, which is the method of any one of the twenty-ninth through the thirty-seventh embodiments, wherein the activator support is fed to a precontactor, wherein the precontactor is configured to receive the polymerization catalyst system via one or more precontactor feed streams, and wherein at least one of the precontactor feed streams comprises at least a portion of the activator support.

A thirty-ninth embodiment, which is the method of the thirty-eighth embodiment, wherein at least one of the precontactor feed streams comprises at least a portion of a catalyst, at least a portion of a co-catalyst, or both.

A fortieth embodiment, which is the method of any one of the twenty-ninth through the thirty-ninth embodiments, wherein at least a portion of a catalyst and at least a portion of a co-catalyst contact each other upstream of the precontactor.

A forty-first embodiment, which is the method of any one of the twenty-ninth through the fortieth embodiments, wherein the activator support is characterized by a precontactor residence time of from about 1 minute to about 60 minutes.

A forty-second embodiment, which is the method of the forty-first embodiment, wherein the reactor feed stream comprises at least a portion of a precontactor feed stream comprising at least a portion of the activator support, and wherein a turbidity of a precontactor feed stream comprising at least a portion of the activator support is averaged over the precontactor residence time to yield an averaged turbidity of the activator support, an averaged concentration of the activator support, or both.

A forty-third embodiment, which is the method of any one of the twenty-ninth through the forty-second embodiments, wherein a mass balance is calculated across the precontactor to yield an amount of activator support in the precontactor.

A forty-fourth embodiment, which is the method of any one of the twenty-ninth through the forty-third embodiments, wherein the activator support is stored in a storage tank upstream of a reactor, and wherein the turbidity of the reactor feed stream is measured downstream of the storage tank.

A forty-fifth embodiment, which is the method of the forty-fourth embodiment, wherein the storage tank is located upstream of a precontactor.

A forty-sixth embodiment, which is the method of the forty-fifth embodiment, wherein the turbidity of the reactor feed stream is measured (i) downstream of the storage tank and upstream of the precontactor; (ii) downstream of the precontactor and upstream of a reactor; or combinations thereof.

A forty-seventh embodiment, which is the method of any one of the twenty-ninth through the forty-sixth embodiments, wherein a mass balance is calculated across the storage tank to yield an amount of the activator support in the storage tank.

A forty-eighth embodiment, which is the method of any one of the twenty-ninth through the forty-seventh embodiments further comprising calculating a ratio of activator support/catalyst, a ratio of activator support/co-catalyst, or both; and comparing the ratio of activator support/catalyst to a target ratio of activator support/catalyst, the ratio of activator support/co-catalyst to a target ratio of activator support/co-catalyst, or both.

A forty-ninth embodiment, which is the method of the forty-eighth embodiment, wherein the ratio of activator support/catalyst is different when compared to the target ratio of activator support/catalyst, and wherein the ratio of activator support/co-catalyst is the same when compared to the target ratio of activator support/co-catalyst, further comprising adjusting the amount of catalyst to meet the target ratio of activator support/catalyst.

A fiftieth embodiment, which is the method of any one of the twenty-ninth through the forty-ninth embodiments, wherein the ratio of activator support/catalyst is the same when compared to the target ratio of activator support/catalyst, and wherein the ratio of activator support/co-catalyst is different when compared to the target ratio of activator support/co-catalyst, further comprising adjusting the amount of co-catalyst to meet the target ratio of activator support/co-catalyst.

A fifty-first embodiment, which is the method of any one of the twenty-ninth through the fiftieth embodiments, wherein the ratio of activator support/catalyst is different when compared to the target ratio of activator support/catalyst, and wherein the ratio of activator support/co-catalyst is different when compared to the target ratio of activator support/co-catalyst, further comprising adjusting the amount of activator support to meet the target ratio of activator support/catalyst and the target ratio of activator support/co-catalyst.

A fifty-second embodiment, which is the method of any one of the twenty-ninth through the fifty-first embodiments, wherein (b) translating the turbidity of the reactor feed stream into a concentration of the solid component in the reactor feed stream further comprises subtracting a background signal of the at least one metallocene from the measured turbidity of the reactor feed stream.

A fifty-third embodiment, which is a method of monitoring a solid component of a reactor feed stream in a polymer production system, comprising: (a) measuring a turbidity of a precontactor feed stream, wherein the precontactor feed stream comprises a solid component of a polymerization catalyst system; and (b) translating the turbidity of the precontactor feed stream into a concentration of the solid component in a precontactor effluent stream, wherein the precontactor effluent stream comprises the reactor feed stream.

A fifty-fourth embodiment, which is the method of the fifty-third embodiment, wherein the solid component comprises an activator support, and wherein the polymerization catalyst system comprises at least one metallocene and an organoaluminum compound.

A fifty-fifth embodiment, which is the method of any one of the fifty-third and the fifty-fourth embodiments further comprising calculating a mass balance across the precontactor to yield an amount of activator support in the precontactor; calculating a ratio of activator support/at least one metallocene, a ratio of activator support/organoaluminum compound, or both; and comparing the ratio of activator support/at least one metallocene to a target ratio of activator support/at least one metallocene, the ratio of activator support/organoaluminum compound to a target ratio of activator support/organoaluminum compound, or both.

A fifty-sixth embodiment, which is a method of monitoring a solid component of a reactor feed stream in a polymer production system, comprising: (a) measuring a turbidity of a precontactor effluent stream, wherein the precontactor effluent stream comprises the reactor feed stream; and (b) translating the turbidity of the precontactor effluent stream into a concentration of the solid component in the reactor feed stream.

A fifty-seventh embodiment, which is the method of the fifty-sixth embodiment, wherein the solid component comprises an activator support, wherein the polymerization catalyst system comprises at least one metallocene and an organoaluminum compound, and wherein the concentration of the at least one metallocene and organoaluminum compound are measured upstream of a precontactor.

A fifty-eighth embodiment, which is the method of the fifty-seventh embodiment, wherein (a) measuring a turbidity of a precontactor effluent stream further comprises subtracting a background signal of the at least one metallocene from the measured turbidity of the precontactor effluent stream.

A fifty-ninth embodiment, which is a polyethylene production system comprising: a polymerization catalyst system comprising at least one catalyst and an activator support, wherein the at least one catalyst, the activator support, or both are a solid component of the polymerization catalyst system; a precontactor configured to receive the polymerization catalyst system via one or more precontactor feed streams, wherein at least one of the precontactor feed streams comprises at least a portion of the solid component; a precontactor effluent stream exiting the precontactor, wherein the precontactor effluent stream comprises at least a portion of the polymerization catalyst system; a polyethylene polymerization reactor configured to receive at least a portion of the precontactor effluent stream as a reactor feed stream, wherein the reactor feed stream comprises at least a portion of the solid component; and at least one turbidimeter for measuring a turbidity of a precontactor feed stream having a solid component therein, a turbidity of a precontactor effluent stream having a solid component therein, or both, wherein the turbidity of the precontactor feed stream, the turbidity of the precontactor effluent stream, or both are translated into a concentration of the solid component in the reactor feed stream.

A sixtieth embodiment, which is the polyethylene production system of the fifty-ninth embodiment further comprising a control system, wherein the control system comprises at least one processor and at least one controller; wherein the at least one processor receives from the at least one turbidimeter a turbidity signal representing the turbidity of the precontactor feed stream, the turbidity of the precontactor effluent stream, or both; wherein the at least one processor translates the turbidity signal into the concentration of the solid component in the reactor feed stream; wherein the at least one processor calculates one or more ratios of components of the polymerization catalyst system using the concentration of the solid component in the reactor feed stream; wherein the at least one processor compares the one or more ratios of components of the polymerization catalyst system to one or more target ratios; wherein the at least one processor, when the one or more ratios of components of the polymerization catalyst system are different when compared to the one or more target ratios, signals the at least one controller; and wherein the at least one controller adjusts an amount of at least one component of the polymerization catalyst system to meet the target ratios.

A sixty-first embodiment, which is the polyethylene production system of the sixtieth embodiment, wherein the control system is a distributed control system.

A sixty-second embodiment, which is the method of the fifteenth embodiment, wherein measuring the turbidity of the reactor feed stream downstream of the storage tank provides near real-time data about the storage tank running empty.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention.

We claim:

1. A method of monitoring a solid component of a reactor feed stream in a polymer production system, comprising:
   (a) measuring a turbidity of the reactor feed stream, wherein the reactor feed stream comprises a solid component of a polymerization catalyst system, wherein the solid component comprises an activator support, wherein the activator support is fed to a precontactor, wherein the precontactor is configured to receive the polymerization catalyst system via one or more precontactor feed streams, and wherein at least one of the precontactor feed streams comprises at least a portion of the activator support; and
   (b) translating the turbidity of the reactor feed stream into a concentration of the solid component in the reactor feed stream, wherein a mass balance is calculated across the precontactor to yield an amount of activator support in the precontactor.

2. The method of claim 1, wherein (b) translating the turbidity of the reactor feed stream into a concentration of the solid component in the reactor feed stream comprises using a calibration curve with known solid component concentration values as a function of measured turbidity.

3. The method of claim 1, wherein (b) translating the turbidity of the reactor feed stream into a concentration of the solid component in the reactor feed stream further comprises subtracting a background signal from the measured turbidity of the reactor feed stream.

4. The method of claim 1, wherein (a) measuring a turbidity of the reactor feed stream comprises passing at least a portion of the feed stream through a turbidimeter, and obtaining an output signal representing turbidity from the turbidimeter.

5. The method of claim 4, wherein the turbidimeter is located downstream of a solid component delivery device, wherein the solid component delivery device provides for intermittent delivery of the solid component into the reactor feed stream.

6. The method of claim 1, wherein the turbidity of the reactor feed stream, the concentration of the solid component in the reactor feed stream, or both are averaged over a time period to yield an averaged turbidity, an averaged concentration, or both.

7. The method of claim 6, wherein the time period is from about 10 seconds to about 4 hours.

8. The method of claim 6, wherein the time period is a residence time of the solid component in a reactor.

9. The method of claim 6, wherein the time period is a residence time of the solid component in the precontactor.

10. The method of claim 9, wherein the turbidity is measured upstream of the precontactor, downstream of the precontactor, or both.

11. The method of claim 9, wherein the activator support is characterized by a precontactor residence time of from about 1 minute to about 60 minutes.

12. The method of claim 11, wherein the reactor feed stream comprises at least a portion of a precontactor feed stream comprising at least a portion of the activator support, and wherein a turbidity of a precontactor feed stream comprising at least a portion of the activator support is averaged over the precontactor residence time to yield an averaged turbidity of the activator support, an averaged concentration of the activator support, or both.

13. The method of claim 1, wherein the activator support is stored in a storage tank upstream of a reactor, and wherein the turbidity of the reactor feed stream is measured downstream of the storage tank.

14. The method of claim 13, wherein a mass balance is calculated across the storage tank to yield an amount of the activator support in the storage tank.

15. The method of claim 13, wherein measuring the turbidity of the reactor feed stream downstream of the storage tank provides near real-time data about the storage tank running empty.

16. The method of claim 1, wherein the concentration of the solid component is used for calculating one or more ratios of components of the polymerization catalyst system; and wherein the one or more ratios of components of the polymerization catalyst system are compared to one or more target ratios.

17. The method of claim 16, wherein the one or more ratios of components of the polymerization catalyst system are different when compared to the one or more target ratios, and wherein an amount of at least one component of the polymerization catalyst system is adjusted to meet the target ratios.

18. A method of monitoring a solid component of a reactor feed stream in a polymer production system, comprising:
(a) measuring a turbidity of a precontactor feed stream, wherein the precontactor feed stream comprises a solid component of a polymerization catalyst system, wherein the solid component comprises an activator support, wherein the activator support is fed to a precontactor; and
(b) translating the turbidity of the precontactor feed stream into a concentration of the solid component in a precontactor effluent stream, wherein the precontactor effluent stream comprises the reactor feed stream, and wherein a mass balance is calculated across the precontactor to yield an amount of activator support in the precontactor.

19. The method of claim 18 further comprising calculating a ratio of activator support/at least one metallocene, a ratio of activator support/organoaluminum compound, or both; and comparing the ratio of activator support/at least one metallocene to a target ratio of activator support/at least one metallocene, the ratio of activator support/organoaluminum compound to a target ratio of activator support/organoaluminum compound, or both.

20. A method of monitoring a solid component of a reactor feed stream in a polymer production system, comprising:
(a) measuring a turbidity of a precontactor effluent stream, wherein the precontactor effluent stream comprises the reactor feed stream, wherein a precontactor effluent stream is recovered from a precontactor; and
(b) translating the turbidity of the precontactor effluent stream into a concentration of the solid component in the reactor feed stream, wherein the solid component comprises an activator support, and wherein a mass balance is calculated across the precontactor to yield an amount of activator support in the precontactor.

21. The method of claim 20, wherein the polymerization catalyst system comprises at least one metallocene and an organoaluminum compound, and wherein the concentration of the at least one metallocene and organoaluminum compound are measured upstream of a precontactor.

* * * * *